US010705085B2

(12) United States Patent
Lee et al.

(10) Patent No.: US 10,705,085 B2
(45) Date of Patent: Jul. 7, 2020

(54) TETHERED LIPOPLEX NANOPARTICLE BIOCHIPS AND METHODS OF USE

(71) Applicant: Ohio State Innovation Foundation, Columbus, OH (US)

(72) Inventors: Ly James Lee, Columbus, OH (US); Kwang Joo Kwak, Dublin, OH (US); Bo Yu, Zhejiang Province (CN); Yun Wu, Columbus, OH (US); Andrew Lee, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 309 days.

(21) Appl. No.: 15/279,545

(22) Filed: Sep. 29, 2016

(65) Prior Publication Data

US 2017/0328904 A1    Nov. 16, 2017

Related U.S. Application Data

(62) Division of application No. 14/044,631, filed on Oct. 2, 2013, now abandoned.

(60) Provisional application No. 61/744,691, filed on Oct. 2, 2012.

(51) Int. Cl.
*G01N 33/569* (2006.01)
*G01N 33/543* (2006.01)

(52) U.S. Cl.
CPC ... *G01N 33/56983* (2013.01); *G01N 33/5432* (2013.01); *Y02A 50/52* (2018.01); *Y02A 50/59* (2018.01); *Y02A 50/60* (2018.01)

(58) Field of Classification Search
None
See application file for complete search history.

(56) References Cited

U.S. PATENT DOCUMENTS

| | | | |
|---|---|---|---|
| 4,342,566 A | 8/1982 | Theofilopoulos et al. | |
| 4,483,929 A * | 11/1984 | Szoka | G01N 33/586 435/7.9 |
| 4,816,567 A | 3/1989 | Cabilly et al. | |
| 5,543,293 A | 8/1996 | Gold et al. | |
| 5,580,737 A | 12/1996 | Polisky et al. | |
| 5,631,146 A | 5/1997 | Szostak et al. | |
| 5,786,462 A | 7/1998 | Schneider et al. | |
| 5,804,440 A | 9/1998 | Burton et al. | |
| 6,096,441 A | 8/2000 | Hauser et al. | |
| 2002/0182717 A1 | 12/2002 | Karlsson | |
| 2004/0023304 A1 | 2/2004 | Stefan et al. | |
| 2005/0244907 A1 * | 11/2005 | Graham | C12Q 1/00 435/8 |

(Continued)

FOREIGN PATENT DOCUMENTS

WO    1994029348 A2    12/1994

OTHER PUBLICATIONS

Bally et al., Lipsome and Lipid Bilayer Arrays Towards Biosensing Applications, 2010, Small, vol. 6, No. 22, pp. 2481-2497.

(Continued)

*Primary Examiner* — Rebecca M Giere
(74) *Attorney, Agent, or Firm* — Standley Law Group LLP; Stephen L. Grant; Jeffrey S. Standley

(57) ABSTRACT

Disclosed are compositions and methods for the use of lipoplex nanoparticle chips and arrays in the detection of/diagnosis of a disease or condition.

13 Claims, 21 Drawing Sheets

Schematic and photos of TLN microarray formation (A) micro-contact printing of SAM on gold coated glass or other substrate, (B) placement of WC_14, (C) passivation with PEG thiol mixture, (D) formation of tethered lipoplex, (E) insertion of antibody, and (F) cell binding on immunoliposome array.

(56) References Cited

U.S. PATENT DOCUMENTS

| | | | | |
|---|---|---|---|---|
| 2010/0022001 | A1* | 1/2010 | Graham | A61K 9/1272 |
| | | | | 435/375 |
| 2010/0240129 | A1* | 9/2010 | Patane | A61K 9/1272 |
| | | | | 435/375 |
| 2011/0033840 | A1* | 2/2011 | Tu | A61K 31/711 |
| | | | | 435/5 |
| 2011/0052671 | A1 | 3/2011 | Zasadzinski et al. | |
| 2011/0059867 | A1 | 3/2011 | Kim et al. | |
| 2012/0202709 | A1* | 8/2012 | Bergo | C40B 30/10 |
| | | | | 506/12 |

OTHER PUBLICATIONS

Boerner et al., Production of antigen-specific human monoclonal antibodies from in vitro-primed human splenocytes, J. Immunol., 1991, 147(1):86-95.
Bruggermann et al., Designer mice: the production of human antibody repertoires in transgenic animals, Year in Immunol., 1993, 7:33-40.
Chaput et al., Exosomes: immune properties and potential clinical implementations, Semin Immunopathol., 2011, 33, 419-440.
Chen et al., Characterization of microRNAs in serum: A novel class of biomarkers for diagnosis of cancer and other diseases, Cell Res., 2008, 18, 997-1006.
Cole et al., The EBV-hybridoma technique and its application to human lung cancer, In: Monoclonal Antibodies and Cancer Therapy (vol. 27, UCLA Symposia on Molecular and Cellular Biology, New Series) (eds. R.A. Reisfeld and S. Sell), pp. 77-96, Alan R. Liss, Inc. N.Y., 1985.
Eisfeld et al., mkR-3151 interplays with its host gene BAALC and independently affects outcome of patients with cytogenically normal acute myeloid leukemia, Blood, 2012, 120, 249-58.
Garzon et al., Targeting microRNAs in cancer: rationale, strategies and challenges, Nat Rev Drug Discovery, 2010, 9, 775-789.
Hall et al., Sensitive detection of DNA polymorphisms by the serial invasive signal amplification reaction, Proc. Natl. Acad. Sci. USA, 2000, 97:8272-8277.
Hangartner et al., Antiviral antibody responses: the two extremes of a wide spectrum, Nat Rev Immunol. 6, 2006, 231-243.
Holland et al., Detection of specific polymerase chain reaction product by utilizing the 5'—3' exonuclease activity of Thermus aquaticus DNA polymerase, Proc. Natl. Acad. Sci. USA, 1991, 88: 7276-7280.
Hoogenboom et al. By passing-immunisation. Human antibodies from synthetic repertoires of germline VH gene segments rearranged in vitro, J. Mol. Biol., 1992, 227:381.
Jakobovits et al., Analysis of homozygous mutant chimeric mice: deletion of the immunoglobulin heavy-chain joining region blocks Bcell development and antibody protection, Proc. Natl. Acad. Sci. USA, 1993, 90:2551:255.
Jakobovits et al., Germ-line transmission and expression of a human-derived yeast artificial chromosome, Nature, 1993, 362:255-258.

Josko, Molecular virology in the clinical laboratory, Clin Lab Sci, 2010, 23. 231-236.
Kohler et al., Continuous cultures of fused cells secreting antibody of predefined specificity, Nature, 1975, 256:495.
Kroh et al., Analysis of circulating microRNA biomarkers in plasma and serum using quantitative reverse transcription-PCR (qRT-PCR), Methods, 2010, 50, 298-301.
Kwak et al., Imaging stretched single DNA molecules by pulsed-force-mode atomic force microscopy, Ultramicroscopy, 2003, 97, 249-255.
Kwak et al., Formation and Finite Element Analysis of Tethered Bilayer Lipid Structures, Langmuir, 2010, 26, 18199-18208.
Marks et al., By-passing immunication. Human antibodies from V-gene libraries displayed on phage, J. Mol. Biol, 1991, 222:581.
McGillivray et al., Molecular-scale structural and functional characterization of sparsely tethered bilayer lipid membranes, Biointerphases, 2007, 2, 21-33.
Mitchell et al., Circulating microRNAs as stable blood-based markers for cancer detection, Proc Natl Acad Sci USA, 2008, 105, 10513-10518.
Moore et al., Why do viruses cause cancer? Highlights of the first century of human tumour virology, Nat Rev Cancer, 2010, 10, 878-889.
Morrison et al., Chimeric human antibody molecules: mouse antigen-binding domains with human constant region domains, Proc. Natl. Acad. Sci. USA, 1984, 81:6851-6855.
Ryan, Cancer: Viruses' backup plan, Nature, 2010, 466, 1054-1055.
Santarius et al., A census of amplified and overexpressed human cancer genes, Nat Rev Cancer, 2010, 10, 59-64.
Schwarzenbach et al., Cell-free nucleic acids as biomarkers in cancer patients, Nat Rev Cancer, 2011, 426-437.
Schweitzer et al., Cell-free nucleic acids as biomarkers in cancer patients, Nat Rev Center, 2011, 11, 426-437.
Shen et al., Diagnosis of lung cancer in individuals with solitary pulmonary nodules by plasma microRNA biomarkers, BMC. Cancer, 2011, 11, 374.
Storch, Diagnostic virology, Clin Infect Dis., 2000, 31, 739-51.
Thery et al., Exosomes: composition, biogenesis and function, Nat Rev Immunol, 2002, 2, 569-579.
Thery et al., Isolation and characterization of exosomes from cell culture supernatants and biological fluids, Curr Protoc Cell Biol, 2006, 3.22.1-322.92.
Valadi et al., Exosome-mediated transfer of mRNAs and microRNAs is a novel mechanism of genetic exchange between cells, Nat Cell Biol., 2007, 9, 654-659.
Warth et al., Large-scale comparative analyses of immunomarkers for diagnostic subtyping of non-small-cell lung cancer biopsies, Histopathology, 2012, 61, 1017-1025.
Wei et al., Identification of plasma microRNA-21 as a biomarker for early detection and chemosensitivity of non-small cell lung cancer, Chin J Cancer, 2011, 6, 407-14.
Weir et al., Characterizing the cancer genome in lung adenocarcinoma, Nature, 2007, 450, 893-898.
Weisman et al., Nanostructure of cationic lipid-oligonucleotide complexes, Biophys. J., 2004, 87, 609-614.
Zoller, New recombinant DNA methodology for protein engineering, Curr. Opin. Biotechnol., 1992, 3:348-354.

* cited by examiner

Schematic and photos of iTLN microarray formation (A) micro-contact printing of SAM on gold coated glass or other substrate, (B) placement of WC_14, (C) passivation with PEG thiol mixture, (D) formation of tethered lipoplex, (E) insertion of antibody, and (F) cell binding on immunoliposome array.

Fluorescence micrographs comparing cell separation efficacy between a conventional antibody microarray and the ITLN microarray. A–D are Raji and Jurkat cell lines with anti-CD20 as the antibody ligand. E–H are MCF-7 and Raji cell lines with EpCAM as the antibody ligand. A, C, E and G are before washing, while B, D, F and H are after washing.

(A) Quantitative comparison of MCF-7 cell capture and non-specific binding of Raji cells using EpCAM based iTLN and antibody arrays at different cell incubation times and antibody concentrations. (B) Fluorescence micrograph showing miR21 detected in captured MCF-7 cells by iTLN microarray containing miR-21 LNA MB and EpCAM antibody.

A schematic diagram showing the concept of a multiplexing iTLN array with microfluidic device for combinatorial design.

A schematic diagram showing the concept of using cTLN microarray to detect the genetic materials in the virus and exosomes as biomarkers for early disease detection

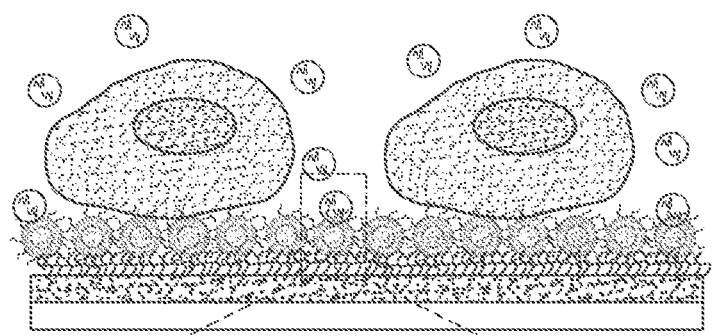
Fig.6a
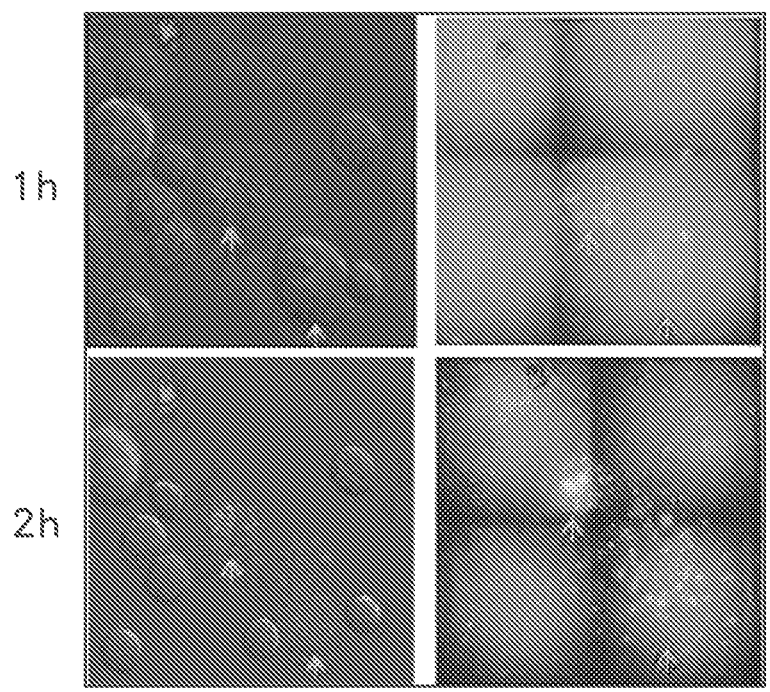
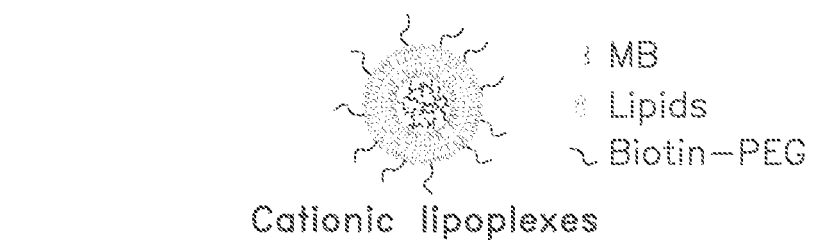
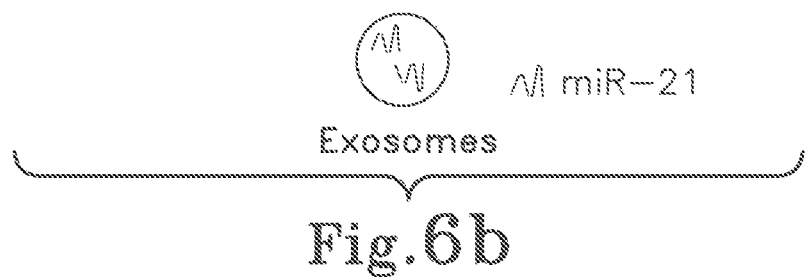
Fig.6b

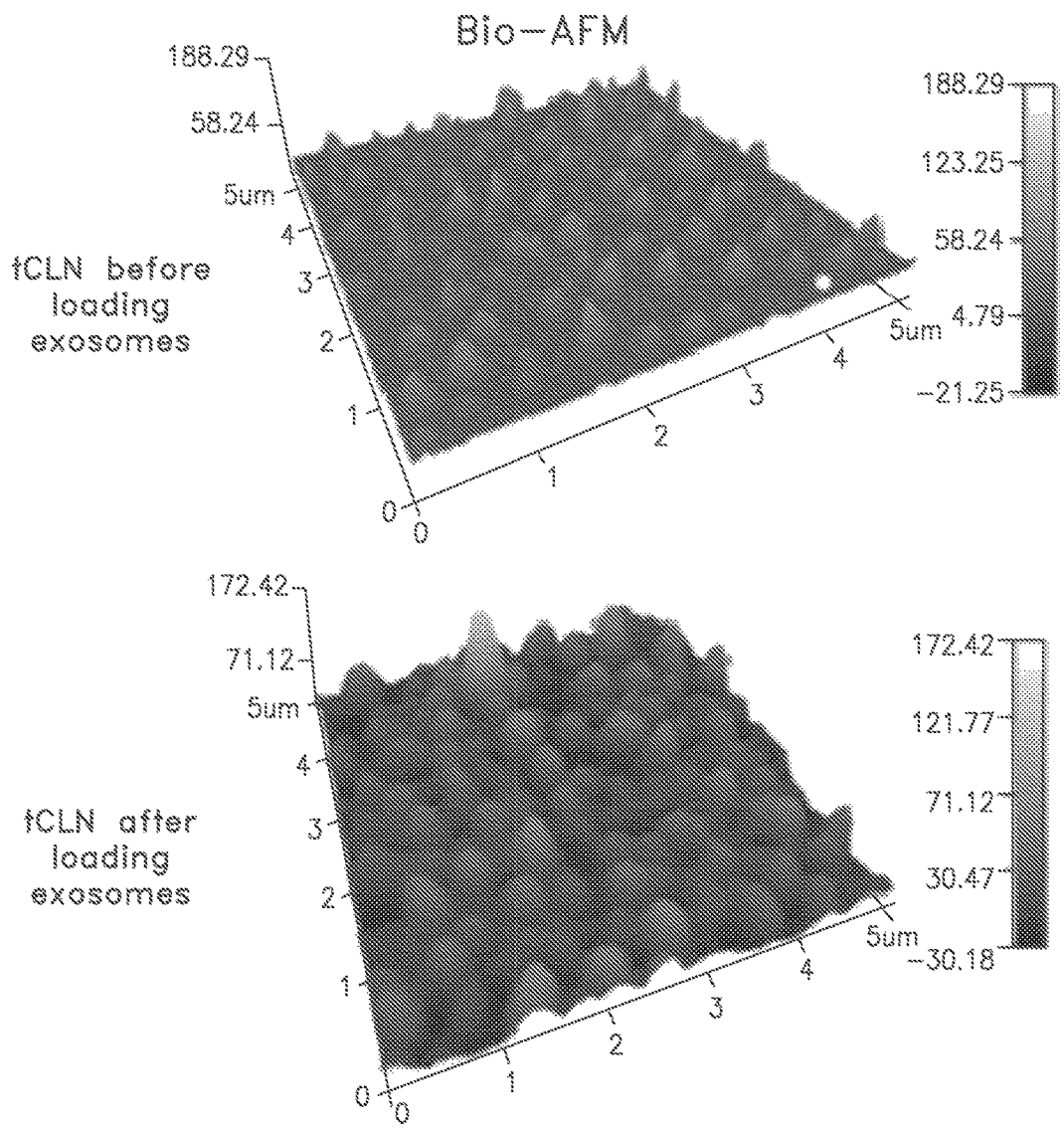

Fig.6c

The release and capture of exosomes released by A549 non-small cell lung cancer cells in real time. 1 hour after A549 cells were applied on the microarray containing miR-21 MB, we did not observe many green fluorescent signals from miR-21 MB on cTLN microarray. However, 2 hours later, we observed lots of green fluorescence emitted by miR-21 MB, suggesting the successful capture and detection of miR-21 containing exosomes released by A549. In addition, we also observed miR-21 MB fluorescence from the A549 cells, suggesting that our microarray can detect miR-21 microRNA expression in both exosomes and cells.

The green fluorescence from miR-181a MB demonstrates the successful capture and detection of miR-181a mRNA inside the lentivirus using our cTLN chips.

Our cTLN microarray shows stronger fluorescence signals of miR-21 microRNA and TTF-1 mRNA in lung cancer patient serum than in a healthy human serum.

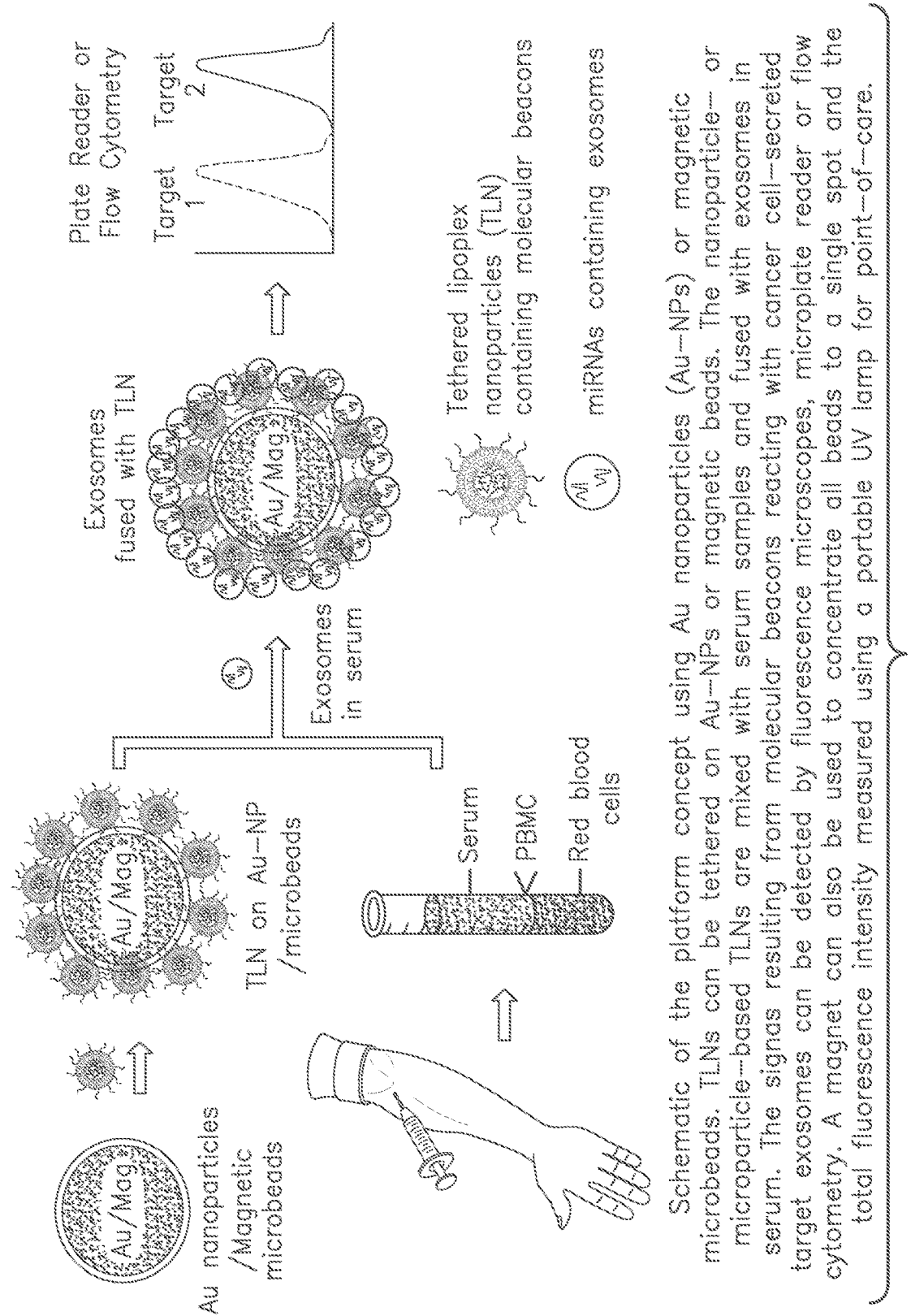

Fig. 10

Schematic of the platform concept using Au nanoparticles (Au-NPs) or magnetic microbeads. TLNs can be tethered on Au-NPs or magnetic beads. The nanoparticle- or microparticle-based TLNs are mixed with serum samples and fused with exosomes in serum. The signals resulting from molecular beacons reacting with cancer cell-secreted target exosomes can be detected by fluorescence microscopes, microplate reader or flow cytometry. A magnet can also be used to concentrate all beads to a single spot and the total fluorescence intensity measured using a portable UV lamp for point-of-care.

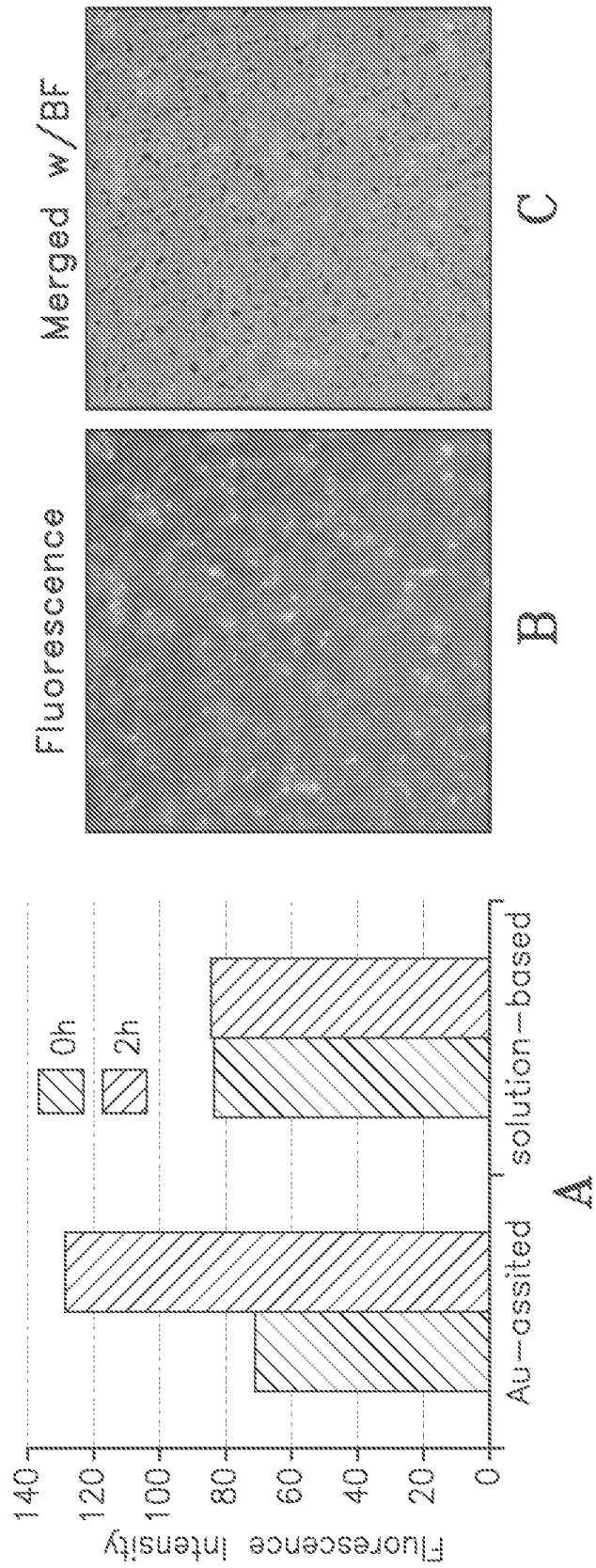

Fig. 11

(A) Quantitative comparison of fluorescence intensity between a conventional solution-based mixing method with cTLNs and exosomes in serum and Au-NP based cTLN method. The Au-NP based method shows significant increase of the fluorescence intensity after incubation at 37°C for 2 h. (B) and (C) Fluorescence micrograph and merged image with bright field, respectively. The micrographs confirm that the Au-NP based method shows higher efficiency of fusion between cTLNs and target exosomes.

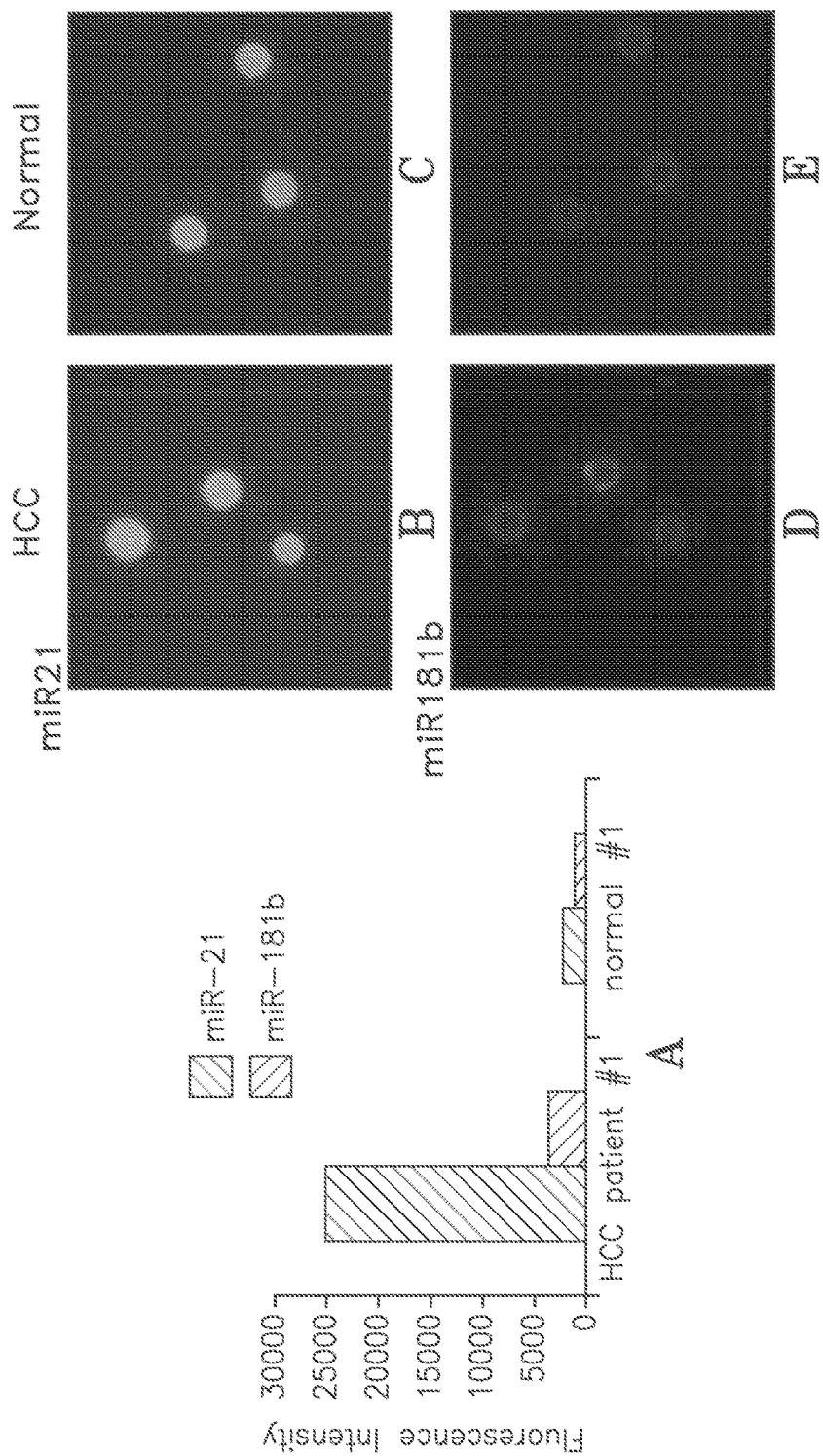

Fig. 12

(A) Quantitative comparison of fluorescence intensity between HCC patient serum and normal donor serum using Au-coated polystyrene magnetic beads. The magnetic beads method shows significant increase of the fluorescence intensity with cTLNs containing miR-21 molecular beacons after incubation at 37°C for 2 h. (B) and (C) Fluorescence micrographs showing the comparison of miR-21 detection between HCC patient and normal donor. (D) and (E) Fluorescence micrographs showing the comparison of miR-181b detection between HCC patient and normal donor.

TETHERED LIPOPLEX NANOPARTICLE BIOCHIPS AND METHODS OF USE

CROSS-REFERENCE TO RELATED APPLICATIONS

This application is a divisional of, and claims a priority benefit to, U.S. application Ser. No. 14/044,631, filed on 2 Oct. 2013, which in turn is entitled to benefit of priority to U.S. provisional application 61/744,691, filed on 2 Oct. 2012. Both applications are incorporated herein by reference as if fully recited.

STATEMENT REGARDING FEDERALLY-SPONSORED R&D

The present invention was made with government support under EEC-0425626 and EEC-0914790 awarded by the National Science Foundation. The Government may have certain rights in the invention.

TECHNICAL FIELD

The disclosure relates to compositions and methods for the use of lipoplex nanoparticle chips and arrays to detect and/or treat a disease or condition.

BACKGROUND

Early and convenient detection has become extremely important against various diseases including cancers and infectious diseases. The earlier a disease is diagnosed, the more likely it can be cured or successfully managed. Although significant progress has been made in disease diagnosis and treatment, mortality rates of diseases such as AIDS and cancer have not changed in the last several decades. One possible reason is the lack of easy, fast, non-invasive and affordable screening tests for early disease detection. Capturing and identifying circulating tumor cells (CTCs) in human blood or body fluid samples, i.e. 'liquid biopsy' has gained a great deal of interest in recent years because of its potential for early and patient friendly cancer detection and monitoring. Antibody and other cell surface ligands have been widely used for cell separation via either magnetic-activated cell sorting (MACS) where ligands are immobilized to magnetic nanoparticles or flow cytometry in fluorescent-activated cell sorting (FACS) where antibodies are labeled with fluorescent dyes. Since flurorophore staining of antibody and immobilization of antibody to magnetic nanoparticles are expensive and time consuming, particularly for multiplexed cell separation, the parallelism and miniaturization inherent in microarray-based cell sorting methods were developed in recent years because they allow a wide variety of cell surface antigen groups to be screened simultaneously in a small area with low ligand and cell needs.

Cellular microarray assays have been used for profiling specific surface antigens expressed on living cancer cells such as leukemia, prostate cancer, antigen specific T cells and stem cells. However, their efficacy is often limited due to weak binding between the target cells and surface coated ligands and the inherent non-specific binding of non-targeted cells. In the aforementioned methods, a separate detection method is needed to analyze intracellular biomarkers of the captured cells. Usually the detection methods require cell lysis or fixing. Thus, there is a need of new detection methods which can identify cells alive so the captured target cells can be used for further analysis or treatment.

SUMMARY

Disclosed are methods and compositions related to the diagnosis/detection of a disease or condition using lipoplex nanoparticle chips and arrays.

In one aspect, disclosed herein are methods of detecting the presence of a disease or condition in a subject comprising obtaining a tissue or body fluid sample from a subject, contacting a lipoplex nanoparticle chip or array with the tissue sample from the subject, wherein the lipoplex comprises a liposome with one or more labeling moieties (for example a molecular beacon or quantum dot) incorporated into the liposome, wherein the lipoplex further comprises a surface targeting moiety (for example, a positive charge, antibody molecules, pepitides, carbohydrates, aptamer, DNA/RNA or their mixtures) on the liposomal surface as receptors for detecting, binding specific target cell, cell secreted microvesicles including exosomes, virus, bacteria, or antigens that corresponds to a particular disease or condition, and detecting the presence or absence of a disease or condition, wherein the presence of a disease or condition is indicated by the excitation of a labeling moiety that occurs through the capture and incorporation of a cell, microvesicles including exosomes, virus, bacteria, or antigen that corresponds to a particular disease or condition into the lipoplex nanoparticle.

In another aspect, disclosed herein are methods of detecting exosomes comprising obtaining a tissue or body fluid sample from a subject, contacting a lipoplex nanoparticle chip or array with the tissue or fluid sample from the subject, wherein the lipoplex comprises a liposome with one or more labeling moieties, wherein the lipoplex further comprises a surface targeting moiety (for example, a positive charge), and wherein the positive charge on the lipoplex nanoparticle surface binds to negatively charged antigens and exosomes, and detecting the presence or absence of a disease or condition, wherein the presence of the exosome is indicated by the excitation of a labeling moiety that occurs through the capture and incorporation of exosomes into the lipoplex nanoparticle.

In another aspect, disclosed herein are Tethered immunolipoplex Nanoparticle (iTLN) or cationic Lipoplex Nanoparticle (cTLN) chips or arrays where intracellular ligands such as MB and cell surface ligands such as antibody are encapsulated and post-inserted respectively in liposomal nanoparticles tethered on a flat surface or nano/micro-scale particle. Since cell binding is enhanced and optimized by utilizing the combined antibody and lipid interactions, the iTLN/cTLN chips/arrays disclosed herein outperform conventional spotted arrays in higher cell binding strength, better separation efficacy and lower antibody consumption. In addition to Circulating Tumor Cell (CTC) capture and identification, the arrays can also be used to capture and identify virus and cell secreted nanoparticles such as microvesicles and exosomes.

Utilizing this concept, uptake and internalization of molecular beacon (MB)-containing iTLNs/cTLNs allows direct detection of intracellular biomarkers in the captured living cells and extracellular nucleic acids or proteins contained inside the virus and cell secreted nanoparticles such as microvesicles and exosomes.

Disclosed herein is a method for preparing a tethered liposome chip or array. As an example, a mixture of 1-thiahexa(ethyleneoxide) lipidic anchor molecule WC14 [20-tetradecyloxy-3,6,9,12,15,18,22-heptaoxahexatricontane-1-thiol] and a lateral spacer β-mercaptoethanol (βME) in ethanol was patterned onto a gold coated and self-assembly monolayer (SAM) covered glass substrate by micro-contact printing using a polydimethylsilosane (PDMS) micropillar array stamp formed by soft lithography.

To prevent nonspecific cell binding, a mixture of polyethylenegylcol (PEG) thiol molecules was introduced to protect the non-disk area. A lipid mixture was used to form the liposome array. The particle sizes of tethered liposomes agreed well with non-tethered ones prepared by the conventional bulk mixing method and analyzed using dynamic light scattering (DLS) goniometry.

To detect intracellular biomarkers in captured living cells, MBs were encapsulated in iTLNs/cTLNs. Other biomolecules, drugs and imaging reagents and their combinations can also be encapsulated in iTLNs/cTLNs. A simple post-insertion method or biotin-avidin method was adopted to incorporate antibody ligands into preformed liposome microarray. In addition to antibody, other ligands, such as peptides, carbohydrates can also be bound onto iTLNs for cell separation.

The iTLN/cTLN chip disclosed herein can be extended to an array where each small area is consisted of specific antibody, peptide, carbohydrate, or their mixture on the nanoparticle surface and specific MB or MB mixture inside the lipoplex nanoparticles. Such multiplexing array allows capture and detection of many target cells, exosomes or virus in a combinatorial design.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 6, presented now over two sheets as FIGS. 6a, 6b and 6c, shows, in FIG. 6a, the release and capture of exosomes released by A549 non-small cell lung cancer cells in real time. As seen at FIG. 6b, 1 hour after the A549 cells were placed on the chip containing miR-21 MB, there were not many green fluorescent signals from miR-21 MB on cTLN chip observed. However, 2 hours later, lots of green fluorescence emitted by miR-21 MB were observed, indicating the successful capture and detection of miR-21 containing exosomes released by A549. In addition, miR-21 MB fluorescence from the A549 cells was observed, indicating that the chip can detect miR-21 microRNA expression in both exosomes and cells, as seen at FIG. 6c.

FIG. 10 shows a schematic of the platform concept using Au nanoparticles (Au-NPs) or magnetic polystyrene microbeads. TLNs can be tethered on Au-NPs or magnetic PS beads. The nanoparticle- or microparticle-assisted TLNs are mixed with serum samples and fused with exosomes in serum. The signal from molecular beacons reacted with cancer cell-secreted target exosomes can be detected by optical microscopes, microplate reader or flow cytometry. A magnet can also be used to concentrate all beads to a single spot and the total fluorescence intensity using portable UV lamp can be observed by naked eyes for point-of-care.

FIG. 11 shows quantitative comparisons and microscopy of the cTLN method. (A) Quantitative comparison of fluorescence intensity between a conventional solution-based mixing method with cTLN and exosomes in serum and Au-NP assisted cTLN method. The Au-NP assisted method shows significant increase of the fluorescence intensity after incubation at 37° C. for 2 hours. (B) and (C) Fluorescence micrograph and merged image with bright field, respectively. The micrographs confirm that the Au-NP assisted method shows higher efficiency of fusion between cTLNs and target exosomes.

FIG. 12 shows quantitative comparisons and microscopy of cTLNs containing miR-181b. (A) Quantitative comparison of fluorescence intensity between HCC patient serum and normal donor serum using Au-coated polystyrene magnetic beads. The magnetic beads method shows significant increase of the fluorescence intensity with TLN containing miR-21 molecular beacons after incubation at 37° C. for 2 hours. (B) and (C) Fluorescence micrographs showing the comparison of miR-21 detection between HCC patient and normal donor. (D) and (E) Fluorescence micrographs showing the comparison of miR-181b detection between HCC patient and normal donor.

(FIG. 13a) Exosomes in serum are captured on the tCLN biochip. Exosomal miR-21 in lung cancer patient serum was identified using TIRF microscopy. (FIG. 13b) Cryo-TEM images show typical structures of an exosome in lung cancer patient serum, a cationic lipoplex nanoparticle (CLN) and the fusion between an exosome and a CLN. The exosome is a spherical vesicle with a single, negatively charged phospholipid bilayer containing proteins and nucleic acids at concentrations that do not noticeably perturb the simple vesicular structure, while the CLN shows a much different 'onion-like' structure with multiple wrapped lipid-MB-lipid layers. (FIG. 13c) Schematic diagram of tCLN biochip fabrication. A 30:70:1 mixture of 1-thiahexa(ethyleneoxide) lipidic anchor molecule WC14 [20-tetradecyloxy-3,6,9,12,15,18,22-heptaoxahexa-tricontane-1-thiol], a lateral spacer β-mercapto-ethanol (βME) in 99.5% ethanol and biotin-PEG$_6$-SH was placed onto a gold coated glass. Avidin was then added and un-reacted avidin was washed away using PBS. The CLN containing MBs were tethered on the substrate surface through biotin-avidin interactions and the unbound CLN were washed away with PBS. (2) The AFM image shows the mean diameter of CLN is ~100 nm.

(FIG. 14a) Schematic diagram showing tCLN interactions with cells and cell secreted exosomes. (FIG. 14b) tCLN and TIRF microscopy detect the presence of miR-21 in A549 and HBEC cells, and their secreted exosomes 2 hours after the A549 cells were applied on the tCLN biochip containing miR-21-specific MBs. The red arrows point to miR-21 detected in exosomes, and the yellow arrows point to miR-21 detected in the cells. Clearly, there are more miR-21 rich exosomes secreted by A549 cells. (FIGS. 14c and d) A4F-MASLS and DLS measurements show cancerous A549 cells secret more and smaller exosomes than normal HBEC cells. (FIG. 14e) Bio-AFM images show the average diameter of the fused exosome-lipoplex particles is 2.5 times that of the original lipoplex nanoparticles before fusion.

(FIG. 15a) TIRF microscopy images of miR-21 and TTF-1 mRNA expressions in A549 and HBEC exosomes. Little fluorescent signal was observed in scramble miR-21 and scramble TTF-1 as expected. (FIGS. 15b and c) Fluorescence intensity distributions of miR-21 and TTF-1 analyzed based on 100 images show that more A549 exosomes have higher miR-21 and TTF-1 expression than HBEC exosomes. (FIGS. 15d and e) Using a low cutoff level, the tCLN biochip provides a similar result as qRT-PCR for miR-21 detection and is more sensitive in detecting TTF-1 mRNA. For tCLN, the fluorescence intensity of a single 80 μm×80 μm image is summed and 100 images are used to calculate the average intensity and variation.

DETAILED DESCRIPTION

Figure 1:
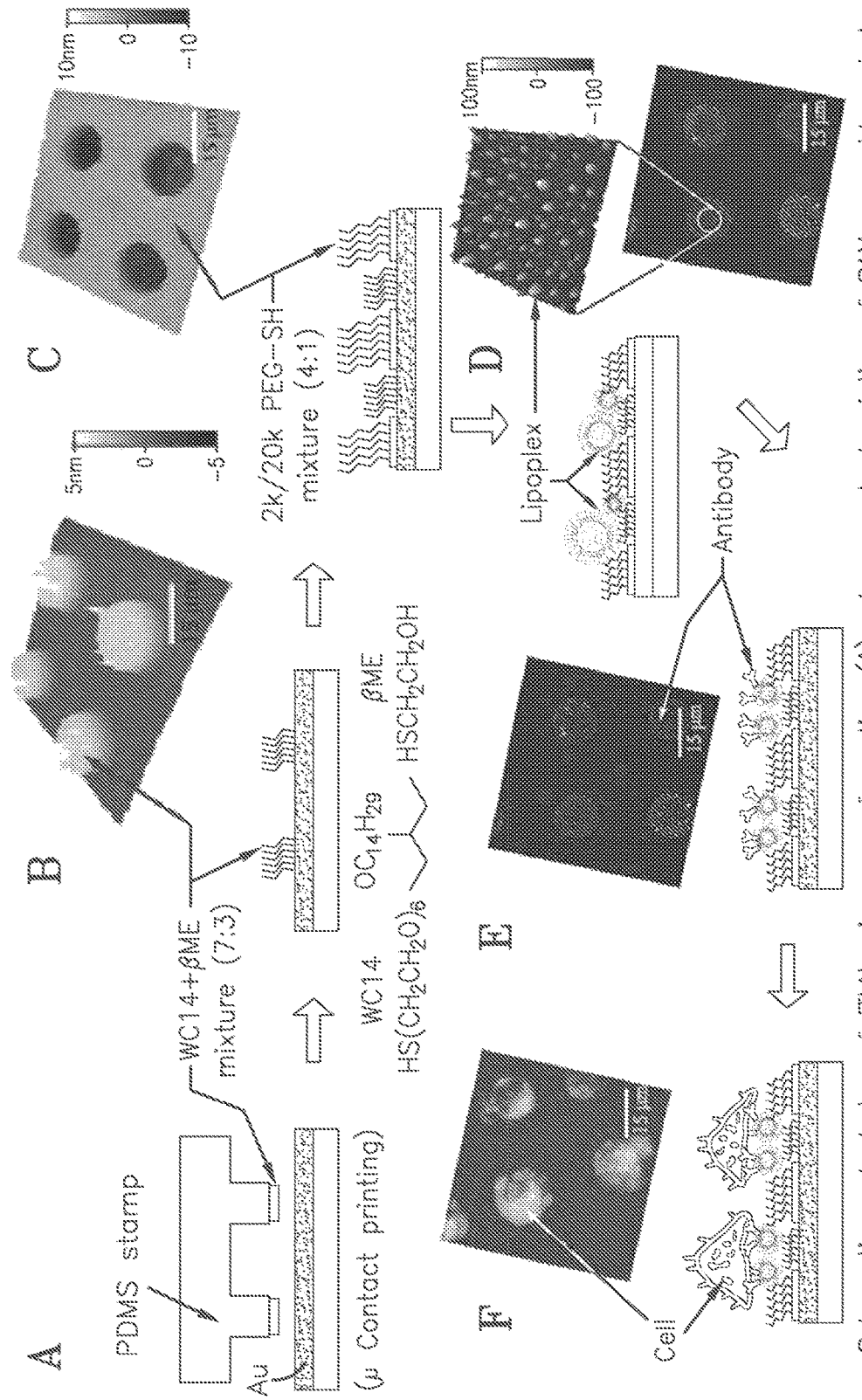
FIG. 1 shows schematic and photos of iTLN microarray formation (A) micro-contact printing of SAM on gold coated glass or other substrate, (B) placement of WC14, (C) passivation with PEG thiol mixture, (D) formation of tethered lipoplex, (E) insertion of antibody, and (F) cell binding on immunoliposome array.
Figure 2:
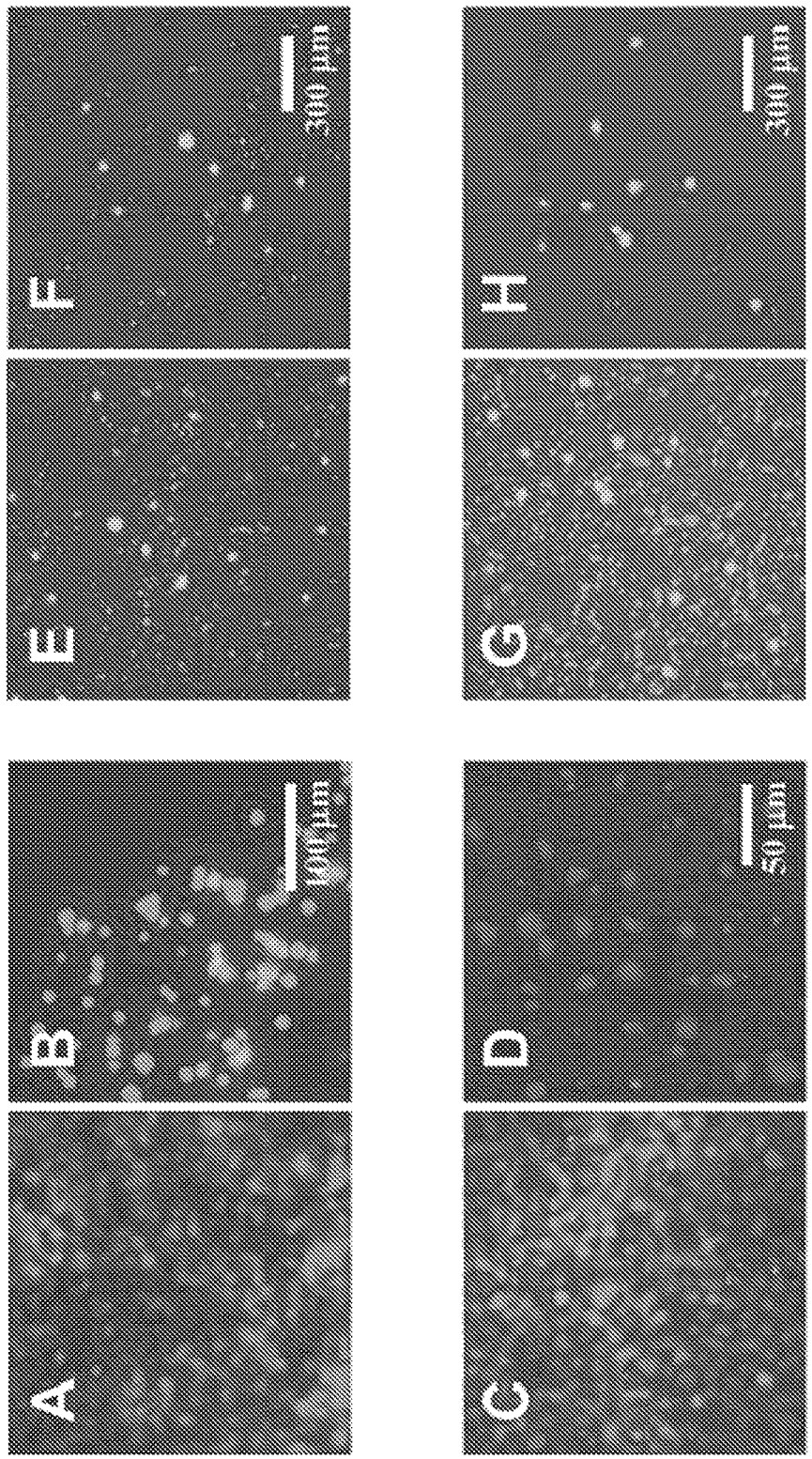
FIG. 2 shows fluorescence micrographs comparing cell separation efficacy between a conventional antibody microarray and the iTLN microarray. A-D are Raji and Jurkat cell lines with anti-CD20 as the antibody ligand. E-H are MCF-7 and Raji cell lines with EpCAM as the antibody ligand. A, C, E and G are before washing, while B, D, F and H are after washing.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Methods of Detecting the Presence of a Disease or Condition

Because current detection/diagnostic methods require cell lysis or fixing there is a need of new detection methods which can identify cells alive so the captured target cells can be used for further analysis or treatment. Disclosed herein are methods of detecting the presence of or diagnosing a disease or condition in a subject comprising the use of a Immuno Liposomol Nanoparticles (iLN) and/or cationic Liposomal Nanoparticle (cLN) chip and array.

In one aspect, disclosed herein are methods detecting the presence of/diagnosing a disease or condition in a subject comprising obtaining a tissue or body fluid sample from a subject, contacting a lipoplex nanoparticle chip or array with the tissue or body fluid sample from the subject, and detecting the presence or absence of a disease or condition. It is understood and herein contemplated that detection of the disease or condition is a diagnosis.

In a further aspect, the methods diagnosing/detecting the presence of a disease or condition in a subject utilize lipoplex nanoparticles disclosed herein. In one aspect the disclosed lipoplex nanoparticles comprise a liposome with one or more labeling moieties (such as, for example, a molecular beacon or quantum dot) incorporated into the liposome. Also disclosed are methods of diagnosing/detecting wherein the lipoplex nanoparticle further comprises a surface targeting moiety (such as, for example a positive charge, antibody molecules, peptides, aptamers, carbohydrates, DNA/RNA or their mixtures) on the liposomal surface as receptors for detecting/binding specific target cell, cell secreted microvesicles including exosomes, virus, bacteria, or antigens that corresponds to a particular disease or condition (i.e, any peptide, polypeptide, protein, or fragment thereof that is part of a bacteria, virus, toxin, or cancer cell or is indicative of the disease or condition despite its origin). Thus, in one aspect, disclosed herein are methods of diagnosing/detecting the presence of a disease or condition comprising obtaining a tissue or body fluid sample from a subject, contacting a lipoplex nanoparticle chip or array with the tissue or body fluid sample from the subject, wherein the lipoplex comprises a liposome with one or more labeling moieties (such as, for example, molecular beacons or quantum dots) incorporated into the liposome, wherein the lipoplex further comprises a surface targeting moiety (for example, a positive charge, antibody molecules, pepitides, carbohydrates, DNA/RNA or their mixtures) on the liposomal surface as receptors for detecting/binding specific target cells, cell secreted microvesicles including exosomes, virus, bacteria, or antigen that corresponds to a particular disease or condition (i.e, any peptide, polypeptide, protein, or fragment thereof that is part of a bacteria, virus, toxin, or cancer cell or is indicative of the disease or condition despite its origin), and detecting the presence or absence of a disease or condition, wherein the presence of a disease or condition is indicated by the excitation of a label of the labeling moiety that occurs through the capture and incorporation into the lipoplex nanoparticle a cell, cell secreted microvesciles including exosomes, virus, bacteria, or antigen that is derived from or causes a particular disease or condition.

Liposome-based chip and array used in the disclosed methods of detection/diagnosis can be prepared by many different methods. It is understood that the liposomes forming a lipoplex nanoparticle can immobilized on the chip/array or free. In one aspect, disclosed herein are methods of detecting/diagnosing a disease or condition comprising contacting a lipoplex nanoparticle chip or array with a tissue or body fluid sample, wherein the lipoplex nanoparticle is immobilized by tethering the lipoplex to the substrate on the chip or array forming a tethered lipoplex nanoparticle (TLN). As disclosed herein, the tethering of the lipoplex nanoparticle can comprise (1) gold coating of a solid substrate with the substrate being glass, silicon wafer, polymer, ceramics or any solid materials; (2) a thin layer of self-assembly monolayer such as 2-mercaptoethanol (β ME), 6-Mercaptohexanol, 16-mercaptohexadecanoic acid (MHA), and other thiol-backfiller molecules; (3) tethering molecules such as WC14, FC16, DC18, and other thiolipids with ethylene oxide units; and (b) preparing tethered liposomal nanoparticles comprising: lipid mixtures such as 1,2-di-O-octadecenyl-3-trimethylammonium propane (DOTMA), 1,2-dioleoyl-3-trimethylammonium-propane (DOTAP), 3β-[N—(N',N'-dimethylaminoethane)-carbamoyl]cholesterol hydrochloride (DC-Cholesterol), and other ionizable lipids, 1,2-di-O-octadecenyl-3-dimethylammonium propane (DODMA), 1,2-dioleoyl-3-dimethylammonium-propane (DODAP), and other non-ionizable lipids: DODMA), L-α-phosphatidylcholine (Egg PC, SoyPC), Cholesterol, 1,2-dipalmitoyl-sn-glycero-3-phosphocholine (DPPC), and other saturated fatty acid, 1,2-dioleoyl-sn-glycero-3-phosphocholine (DOPC), and other helper lipids and 1,2-distearoyl-sn-glycero-3-phosphoethanolamine-N-[methoxy(polyethylene glycol)] (DSPE-PEG), and other PEG phospholipids.

In one aspect, the disclosed lipoplex nanoparticles used in the chip and array can comprise a surface mounted targeting moiety that acts as a receptor that is specific for and binds to an antigen in the tissue sample. These lipoplex nanoparticles, termed immnolipoplex nanoparticles (iLNs) can be part of a tethered (iTLN) or free lipoplex nanoparticles (iFLN) system. The targeting moiety can comprise one or more antibody molecules, pepitides, carbohydrates, DNA/RNAs or their mixtures thereof as receptorss for detecting/binding specific cell surface receptors, target cells, cell secreted microvesicles including exosomes, virus, bacteria, or antigen that corresponds to a particular disease or condition (i.e, any peptide, polypeptide, protein, or fragment thereof that is part of a bacteria, virus, toxin, or cancer cell or is indicative of the disease or condition despite its origin). It is understood that these receptors can be inserted after formation of lipoplex nanoparticle or incorporated into the liposome prior to lipoplex nanoparticle formation. Alternatively, the antibodies, peptides, carbohydrates, DNA/RNAs or mixtures thereof can be attached to the lipoplex nanoparticle through avidin-biotin, digoxigenin (Dig)-anti-Dig, fluorescein-anti-FITC or other hapten linkages. Thus, disclosed herein are methods of diagnosing/detecting the presence of a disease or condition in a subject comprising obtaining a tissue or body fluid sample from a subject, contacting a lipoplex nanoparticle chip or array with the tissue or body fluid sample from the subject, and detecting the presence or absence of a disease or condition, wherein the receptor on the surface of the lipoplex nanoparticle (for example, an antibody) is specific for an antigenic determinant on an exosome, protein, RNA, DNA, viral-like particle, virus, bacterial protein, bacteria, toxin, circulating tumor cell, or viral protein.

In one aspect, the lipoplex nanoparticle does not have a surface receptor for binding to a target but utilizes the positive cationic charge of the liposome to attract and bind negatively charged antigens, such as, for example, exosomes in the tissue or body fluid sample. These lipoplex nanoparticles are termed cationic lipoplex nanoparitcles (cLNs) and like the immunolipoplex nanoparticles can be tethered (cTLN) or free (cFLN). Prior to the present disclosure, the detection of exosomes was extremely difficult due in part to the complexity of body fluids, physical separation of exosomes from cells, and the existance of similar sized particles. Also, because exosomes are typically below 100 nm in size they have a low refractive index that makes them unsuitable for other detection techniques. By contrast, due to the negative charge on exosomes, the disclosed cationic lipoplex nanoparticles will bind to exosomes in a tissue or body fluid sample and this binding results in excitation of the molecular beacon or quantum dot thus allowing for detection. Therefore, in one aspect and in addition to the disclosed methods of diagnosing and detecting the presence of a disease or condition, also disclosed are methods of detecting exosomes comprising obtaining a tissue or body fluid sample from a subject, contacting a lipoplex nanoparticle chip or array with the tissue sample from the subject, and detecting the presence or absence of a disease or condition, wherein the positive charge on the lipoplex nanoparticle surface binds to negatively charged antigens and exosomes.

In one aspect, disclosed herein are disclosed are methods of detecting exosomes comprising obtaining a tissue or body fluid sample from a subject, contacting a lipoplex nanoparticle chip or array with the tissue or fluid sample from the subject, wherein the lipoplex comprises a liposome with one or more labeling moieties, wherein the lipoplex further comprises a surface targeting moiety (for example, a positive charge), and wherein the positive charge on the lipoplex nanoparticle surface binds to negatively charged antigens and exosomes, and detecting the presence or absence of a disease or condition, wherein the presence of the exosome is indicated by the excitation of a labeling moiety that occurs through the capture and incorporation of exosomes into the lipoplex nanoparticle.

It is disclosed and herein contemplated that the disclosed lipoplex nanoparticle chips and arrays can be comprised of a single or multiple arrays. For example, disclosed herein are lipoplex nanoparticle arrays comprising two or more smaller arrays with each array comprising a specific target such as a protein, cell surface target, peptide, RNA, DNA, virus, bacteria, toxin, or exosome. It is further understood that the disclosed arrays can comprise multiple immunolipoplex nanoparticle arrays, cationic lipoplex nanoparticle arrays, or combinations thereof. Thus, in one aspect disclosed herein are methods of detecting the presence of/diagnosing a disease or condition comprising obtaining a tissue or body fluid sample from a subject, contacting a lipoplex nanoparticle array with the tissue or body fluid sample from the subject, and detecting the presence or absence of a disease or condition, wherein the lipoplex nanoparticle array comprises two or more smaller arrays with each small array comprising a specific target. Such methods including arrays, wherein the array comprises one or more iLN arrays, one or more cLN arrays, or any combination or multiple thereof.

It is understood that the antigen can be a viral antigen or virus. Viral antigens can include any peptide, polypeptide, or protein from a virus. Thus in one embodiment the antigen can be an antigen from a virus selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A (including H1N1 or other Swine H1), Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed are methods wherein the antigen is a bacterial antigen or bacteria. The antigen, for example, can be a peptide, polypeptide, or protein selected from the group of bacteria consisting of *M. tuberculosis, M. bovis, M. bovis* strain BCG, BCG substrains, *M. avium, M. intracellulare, M. africanum, M. kansasii, M. marinum, M. ulcerans, M. avium* subspecies paratuberculosis, *Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydiatrachomatis, Chlamydia psittaci, Coxiella burnetti*, other Rickettsial species, *Ehrlichia* species, *Staphylococcus aureus, Staphylococcus epidermidis, Streptococcus pneumoniae, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species.

Also disclosed are methods wherein the antigen is a toxin. It is understood that such toxins can include but are not limited to Abrin, Conotoxins Diacetoxyscirpenol Bovine spongiform encephalopathy agent, Ricin, Saxitoxin, Tetrodotoxin, epsilon toxin, Botulinum neurotoxins, Shigatoxin, Staphylococcal enterotoxins, T-2 toxin, Diphtheria toxin, Tetanus toxoid, and pertussis toxin. In another aspect the disclosed methods can be used to detect/diagnose the presence of a cancer. Thus, disclosed herein are methods wherein the antigen is a cancer-related antigen such as a cancer cell (e.g., a circulating tumor cell), exosome, or cancer protein. The antigen can be, for example, a peptide, polypeptide, or protein selected from the group of cancers consisting of lymphomas (Hodgkins and non-Hodgkins), B cell lymphoma, T cell lymphoma, myeloid leukemia, leukemia, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, pancreatic cancer, or cancer caused cachexia.

It is understood that the disclosed iTLN and cTLN chips, microarrays, arrays and particles capture target cells, microvesicles, exosomes and/or virus with the contained mRNAs, microRNAs and/or proteins and the binding of said iTLN and/or cTLN can be detected by molecular probes such as molecular beacons using any known detection method known in the art including but not limited to total internal reflective fluorescence (TIRF) microscope, fluorescence microscope, plate reader or portable fluorescence detector.

The disclosed methods utilize tissue and body fluid samples obtained from a subject. As used herein "subject" can refer to any human, non-human primate, dog, cat, cow, horse, pig, rat, mouse, gerbil, guinea pig, or fish. A subject can include but is not limited to a patient having previously been diagnosed with a general condition but in need of specific diagnosis. The tissue and body fluid samples obtained as part of or for use in the disclosed methods of detecting/diagnosis can include but are not limited to blood (including peripheral blood and peripheral blood mononuclear cells), serum, plasma, sputum, saliva, urine, tissue biopsy samples (e.g., spleen, liver, bone marrow, thymus, lung, kidney, brain, salivary glands, skin, lymph nodes, and intestinal tract), and specimens acquired by pulmonary lavage (e.g., bronchoalveolar lavage (BAL)). It is understood and herein contemplated that due to the specificity of the lipoplex nanoparticle chips and arrays, purification of samples such as blood are not necessary. Thus, while serum can be separated from a blood sample and run on the chip and array, the separation is not required.

Methods of Making Tethered Lipoplex Nanoparticle Arrays.

It is understood and herein contemplated that the lipoplex nanoparticle arrays disclosed herein and used in the disclosed methods of diagnosis/detection can be free or tethered to a substrate. In one aspect disclosed herein are methods of making a tethered lipoplex nanoparticle array such as, for example, a tethered immunolipoplex nanoparticle array (iTLN) or a tethered cationic lipoplex nanoparticle array (cTLN).

In one aspect the substrate can be composed of any substance suitable for use as a substrate including but not limited to glass, silicon wafer, polymer, ceramics or any solid materials. Such materials can be coated with gold. Thus, in one aspect, disclosed herein are methods of making tethered immunolipoplex nanoparticle (iTLN) and cationic nanoparticle (cTLN) biochips comprising: (a) surface tethering treatment comprising: (1) gold coating of a solid substrate with the substrate being glass, silicon wafer, polymer, ceramics or any solid materials; a thin layer of self-assembly monolayer; and tethering molecules; and preparing the tethered liposomal nanoparticle. In one aspect, 2-mercaptoethanol (13 ME), 6-Mercaptohexanol, 16-mercaptohexadecanoic acid (MHA), and other thiol-backfiller molecules can be used for the self-assembly monolayer. Tethering molecules can include any molecules suitable for the purpose including but not limited to WC14, FC16, DC18, and other thiolipids with ethylene oxide units. Thus, in one aspect disclosed herein are methods method of making tethered immunolipoplex nanoparticle (iTLN) and cationic nanoparticle (cTLN) biochips comprising: (a) surface tethering treatment comprising: (1) gold coating of a solid substrate with the substrate being glass, silicon wafer, polymer, ceramics or any solid materials; (2) a thin layer of self-assembly monolayer such as 2-mercaptoethanol (β ME), 6-Mercaptohexanol, 16-mercaptohexadecanoic acid (MHA), and other thiol-backfiller molecules; and (3) tethering molecules such as WC14, FC16, DC18, and other thiolipids with ethylene oxide units; and preparing the tethered liposomal nanoparticle.

The tethered liposomal nanoparticle can be tethered through the use of a lipid mixture including but not limited to 1,2-di-O-octadecenyl-3-trimethylammonium propane (DOTMA), 1,2-dioleoyl-3-trimethylammonium-propane (DOTAP), 3β-[N—(N',N'-dimethylaminoethane)-carbamoyl]cholesterol hydrochloride (DC-Cholesterol), and other ionizable lipids, 1,2-di-O-octadecenyl-3-dimethylammonium propane (DODMA), 1,2-dioleoyl-3-dimethylammonium-propane (DODAP), and other non-ionizable lipids: DODMA), L-α-phosphatidylcholine (Egg PC, SoyPC), Cholesterol, 1,2-dipalmitoyl-sn-glycero-3-phosphocholine (DPPC), and other saturated fatty acid, 1,2-dioleoyl-sn-glycero-3-phosphocholine (DOPC), and other helper lipids and 1,2-distearoyl-sn-glycero-3-phosphoethanolamine-N-[methoxy(polyethylene glycol)] (DSPE-PEG), and other PEG phospholipids. Thus, in one aspect, disclosed herein are methods of making tethered immunolipoplex nanoparticle (iTLN) and cationic nanoparticle (cTLN) biochips comprising: (a) surface tethering treatment comprising: (1) gold coating of a solid substrate with the substrate being glass, silicon wafer, polymer, ceramics or any solid materials; a thin layer of self-assembly monolayer such as 2-mercaptoethanol (β ME), 6-Mercaptohexanol, 16-mercaptohexadecanoic acid (MHA), and other thiol-backfiller molecules; tethering molecules such as WC14, FC16, DC18, and other thiolipids with ethylene oxide units; (b) preparing tethered liposomal nanoparticles comprising: (1) lipid mixtures such as 1,2-di-O-octadecenyl-3-trimethylammonium propane (DOTMA), 1,2-dioleoyl-3-trimethylammonium-propane (DOTAP), 3β-[N—(N',N'-dimethylaminoethane)carbamoyl]cholesterol hydrochloride (DC-Cholesterol), and other ionizable lipids, 1,2-di-O-octadecenyl-3-dimethylammonium propane (DODMA), 1,2-dioleoyl-3-dimethylammonium-propane (DODAP), and other non-ionizable lipids: DODMA), L-α-phosphatidylcholine (EggPC, SoyPC), Cholesterol, 1,2-dipalmitoyl-sn-glycero-3-phosphocholine (DPPC), and other saturated fatty acid, 1,2-dioleoyl-sn-glycero-3-phosphocholine (DOPC), and other helper lipids and 1,2-distearoyl-sn-glycero-3-phosphoethanolamine-N-[methoxy(polyethylene glycol)] (DSPE-PEG), and other PEG phospholipids.

In one aspect, the iTLN are functionalized by post-insertion of antibody molecules, peptide, carbohydrate, DNA/RNA or their mixtures as surface targeting moieties for detecting/biding specific cell surface receptors, target cells, cell secreted microvesicles including exosomes, virus, bacteria, or antigen that corresponds to a particular disease or condition or by avidin-biotin, digoxigenin (Dig)-anti-Dig, fluorescein-anti-FITC or other hapten linkages of antibody molecules, peptide, carbohydrate, DNA/RNA or their mixtures as ligands for detecting/biding specific cell surface receptors, target cells, cell secreted microvesicles including exosomes, virus, bacteria, or antigen that corresponds to a particular disease or condition.

It is understood and herein contemplated that the lipoplex nanoparticles will need to be detected. In one aspect, this detection can occur through the use of molecular beacons, quantum dots, and/or other sensing molecules and particles as ligands for detecting intra-cellular biomarkers such as messenger RNA, microRNA and proteins. Therefore, in one aspect, disclosed herein are methods of making a tethered lipoplex nanoparticle chip and array wherein said iTLN/cTLN nanoparticles contain reagents or reagent mixtures such as molecular beacons, quantum dots, and/or other sensing molecules and particles as ligands for detecting intra-cellular biomarkers such as messenger RNA, microRNA and proteins.

Also disclosed are methods wherein said iTLN/cTLN nanoparticles contain reagents or reagent mixtures such as drug, DNA/RNA, magnetic particles and/or other therapeutic molecules and particles.

It is understood and herein contemplated that the iTLN/cTLN nanoparticles are placed in the form of microarray. It is further contemplated that said iTLN/cTLN nanoparticles are placed in a larger array comprising many smaller microarray with each small array containing specific cell surface targeting ligands, intra-cellular biomarker ligands and/or therapeutic molecules/particles. Such smaller microarrays can comprise any combination of iTLN and/or cTLN.

In a further aspect said iTLN/cTLN chip or array is connected to a microfluidic setup so cell mixtures can be brought onto the array and cell washing can be carried out after certain cell incubation time.

In one aspect, the iTLNs/cTLNs are tethered on nanoscale or microscale particles such as gold or magnetic particles and polymer beads.

It is understood that the disclosed iTLN and cTLN chips, microarrays, arrays and particles capture target cells, microvesicles, exosomes and/or virus with the contained mRNAs, microRNAs and/or proteins and the binding of said iTLN and/or cTLN can be detected by molecular probes such as molecular beacons using a total internal reflective fluorescence (TIRF) microscope, fluorescence microscope, plate reader or portable fluorescence detector.

Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The methods of detection/diagnosis disclosed herein comprise the use of lipoplex nanoparticle chips and arrays. It is understood and herein contemplated that the lipoplex nanoparticles can be immobilized or tethered to a substrate (TLN) or allowed to move freely (FLN). It is further understood that the lipoplex nanoparticle can comprise an antibody, aptamer, functional nucleic acid, RNA, DNA, protein, peptide, carbohydrate or mixture thereof to bind to a target ligand.

Once bound, the target needs to be detected. Therefore, the disclosed lipoplex nanoparticles further comprise means of detection. In one aspect, the disclosed lipoplex nanoparticles can comprise a labeling moiety such as, for example, a molecular beacon or quantum dot that has a label that can be excited for target detection. For example, excitation can occur as a result of hybridization of a targeting moiety or target to the labeling moiety. As used herein, a label can include a radio label, enzyme-linked detection systems, antibody-mediated label detection, fluorescent labels and dyes, fluorescent change probes and primers (for example, molecular beacons, Amplifluors, FRET probes, hairpin quenched probes, cleavable FRET probes, TaqMan probes, scorpion primers, fluorescent triplex oligos, fluorescent water-soluble conjugated polymers, PNA probes and QPNA probes), a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores), radiolables, and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorescent change probes and fluorescent change primers refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos, fluorescent water-soluble conjugated polymers, PNA probes and QPNA probes.

Fluorescent change probes and primers can be classified according to their structure and/or function. Fluorescent change probes include hairpin quenched probes, cleavage quenched probes, cleavage activated probes, and fluorescent activated probes. Fluorescent change primers include stem quenched primers and hairpin quenched primers. The use of several types of fluorescent change probes and primers are reviewed in Schweitzer and Kingsmore, Curr. Opin. Biotech. 12:21-27 (2001). Hall et al., Proc. Natl. Acad. Sci. USA 97:8272-8277 (2000), describe the use of fluorescent change probes with Invader assays.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes (Holland et al., Proc. Natl. Acad. Sci. USA 88:7276-7280 (1991)) are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350☐; Alexa Fluor 430☐; Alexa Fluor 488☐; Alexa Fluor 532☐; Alexa Fluor 546☐; Alexa Fluor 568☐; Alexa Fluor 594☐; Alexa Fluor 633☐; Alexa Fluor 647☐; Alexa Fluor 660☐; Alexa Fluor 680 ☐; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG☐☐CBQCA; ATTO-TAG☐☐FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO☐☐-1; BOBO☐-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FI; Bodipy FL ATP; Bodipy FI-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO☐☐-1; BO-PRO☐☐-3; Brilliant Sulphoflavin FF; BTC; BTC-5N; Calcein; Calcein Blue; Calcium Crimson–; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue☐; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2☐; Cy3.1 8; Cy3.5☐; Cy3☐; Cy5.1 8; Cy5.5☐; Cy5☐; Cy7☐; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrohodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DiIC18(5)); DIDS; Dihydorhodamine 123 (DHR); DiI (DiIC18(3)); I Dinitrophenol; DiO (DiOC18(3)); DiR; DiR (DiIC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43☐; FM 4-46; Fura Red☐☐ (high pH); FuraRed☐/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin EBG; Oregon Green☐; Oregon Green☐☐488; Oregon Green☐ 500; Oregon Green☐☐514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine; Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP☐☐ (super glow BFP); sgGFP☐☐ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red☐; Texas Red-X☐☐ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5;

TOTO-1; TOTO-3; TriColor (PE-Cy5); TRITC TetramethylRodamineIsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two-step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, cations, single domains, engineered scaffolds, peptides, DNA, RNA, nucleic acid aptamers or mixtures thereof, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in E. coli, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

The disclosed lipoplex nanoparticles can comprise probes, which are capable of interacting with a target nucleic acid or protein. "Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

The size of the probes for interaction with the nucleic acids in certain embodiments can be any size that supports the desired enzymatic manipulation of the probe, such as the simple hybridization of the probe. A typical probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a probe can be less than or equal to 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA, DNA, or RNA of any target nucleic acids or they can interact with the polypeptide encoded by any of the target nucleic acids. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, 10, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophilline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with kds from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamers have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate.

Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialized chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include colour coding for microbeads (Luminex, Austin, Tex.; Bio-Rad Laboratories) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of lipoplexes involves both the coupling reagent and the nature of the surface being coupled to. A good array support surface is chemically stable before and after the coupling procedures, allows good spot morphology, displays minimal nonspecific binding, does not contribute a background in detection systems, and is compatible with different detection systems. The immobilization method used are reproducible, applicable to lipoplexes of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of lipoplex immobilization are used and have various pros and cons. Passive adsorption to surfaces is methodologically simple, but allows little quantitative or orientational control; it may or may not alter the functional properties of the lipoplex, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of lipoplex arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatized with phenyldiboronic acid, and salicylhydroxamic acid immobilized on the support surface. This also has low background binding and low intrinsic fluorescence and allows the immobilized protein to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilized on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85sq microns, equivalent to 25 million spots per sq cm, at the limit for optical detection; their readout methods are fluorescence and atomic force microscopy (AFM).

Antibodies

Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen. As used herein, the term "antibody or fragments thereof" encompasses chimeric antibodies and hybrid antibodies, with dual or multiple antigen or epitope specificities, and fragments, such as F(ab')2, Fab', Fab, Fv, sFv, and the like, including hybrid fragments. Thus, fragments of the antibodies that retain the ability to bind their specific antigens are provided. Such antibodies and fragments can be made by techniques known in the art and can be screened for specificity and activity according to the methods set forth in the Examples and in general methods for producing antibodies and screening antibodies for specificity and activity. Also included within the meaning of "antibody or fragments thereof" are conjugates of antibody fragments and antigen binding proteins (single chain antibodies) as described.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human Antibodies

The disclosed human antibodies can be prepared using any technique. Examples of techniques for human monoclonal antibody production include those described by Cole et al. (*Monoclonal Antibodies and Cancer Therapy,* Alan R. Liss, p. 77, 1985) and by Boerner et al. (*J. Immunol.,* 147(1):86-95, 1991). Human antibodies (and fragments thereof) can also be produced using phage display libraries (Hoogenboom et al., *J. Mol. Biol.,* 227:381, 1991; Marks, et al., *J. Mol. Biol.,* 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362: 255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed herein are kits comprising lipoplex nanoparticles; detection antibodies, peptide, carbohydrate, DNA/RNA or mixtures thereof, and optionally avidin-biotin, digoxigenin (Dig)-anti-Dig, fluorescein-anti-FITC or other hapten linkages.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in degrees C. or is at ambient temperature, and pressure is at or near atmospheric.

Example 1: Fabrication of a iTLN Microarray

This example describes a simple method for preparing the tethered immunoliposome microarray. FIG. 1 shows the schematic of the fabrication process with atomic force microscopy (AFM) and fluorescence microscopy photos of structures formed after each individual fabrication step. In FIG. 1A, a 8:2 mixture of 1-thiahexa(ethyleneoxide) lipidic anchor molecule WC14 [20-tetradecyloxy-3,6,9,12,15,18,22-heptaoxahexatricontane-1-thiol] and a lateral spacer β-mercaptoethanol (β ME) in ethanol was patterned onto a gold coated and self-assembly monolayer (SAM) covered glass substrate by micro-contact printing using a polydimethylsilosane (PDMS) micropillar array stamp formed by soft lithography. The AFM image in FIG. 1B shows the 15 µm disk array and the height of the patterned area is about 4 nm.

To prevent nonspecific cell binding, a 80:20 mixture of polyethylenegylcol (PEG) thiol molecules with 2,000 and 20,000 dalton molecular weight was introduced to protect the 80% non-disk area. The AFM image in FIG. 1C shows the height of PEG is about 10 nm.

A lipid mixture of 10 mg/ml [egg phosphatidylcholine (Egg PC): Cholesterol (Chol): methoxy-PEG (MW~2,000 Da)-distearoyl phosphatidylethanolamine (PEG-DSPE)=68:30:2 molar ratio] was used to form the liposome array in FIG. 1D. The AFM image (FIG. 1E) shows the average diameter of liposome around 100 nm and the fluorescence microscopy image (FIG. 1F) shows the liposome microarray at a large scale using green-dye-labeled DSPE. The particle sizes of tethered liposomes agreed well with non-tethered ones prepared by the conventional bulk mixing method and analyzed using dynamic light scattering (DLS) goniometry.

To detect intracellular biomarkers in captured living cells, MBs were encapsulated in iTLNs. A simple post-insertion method was adopted to incorporate antibody ligands into preformed liposome microarray and the first sulfhydryl modified antibodies against the epithelial cell adhesion molecule (EpCAM) reacted with micelles of Mal-PEG-DSPE, and then the product, anti-EpCAM-PEG-DSPE iTLNs were further modified with rhodamine molecule (red color). The Rhodamine-Ab-PEG-DSPE molecule was incubated in phosphate saline (PBS) on the liposome microarray for 1 hour at 37° C. After incubation the unbounded Rhodamine Ab-PEG-DSPE molecules were washed away with PBS solution and the post-inserted immunoliposome nanoparticle (iLN) microarray was taken with fluorescence microscopy as shown in FIG. 1E shows the fluorescence image of the post-inserted iTLN microarray, while FIG. 1F shows the captured anti-EpCAM-positive breast cancer cell line MCF-7 cells. In the current design, 15 µm spots are printed on 1 $cm^2$ area. The PEG area counts about 80% of the total surface.

Example 2: Separation of Raji Cells from Jurkat Cells with Anti-CD20 as the Antibody Ligand This example includes sorting of the Raji Burkitt's lymphoma of B cell type from the Jurkat acute leukemia cell line of T lymphocyte cells. The B-cell specific Rituaxima (anti-CD20) was applied as the cell surface ligand. FIG. 2A-D shows fluorescence microscopy images of captured cells on both conventional antibody and iTLN microarrays. It is clear that the efficacy of cell separation is much better in iTLN microarrays.

Example 3: Separation of MCF-7 Cells from Raji Cells with EpCAM as the Antibody Ligand This example is aimed at potential applications of isolation of rare cells such as circulating tumor cells (CTCs) from blood samples because it is highly valuable for early clinical diagnosis and non-invasive prognosis of cancer metastasis, but remains a tremendous challenge due to the extremely low number of CTCs (~1 in $10^9$ hematologic cells) in the blood of patients.

Since CTCs typically express the epithelial-cell adhesion molecule (EpCAM) on the surface whereas normal hematologic cells do not, substrates with immobilized antibody against EpCAM have been used to isolate CTCs from patient bloods.

Here, a breast cancer cell line, MCF-7 was targeted from Raji cells using anti-EpCAM as the cell surface ligand and miR-21 LNA MB as the intracellular ligand because miR-21 is over expressed in breast cancer cells and can serve as a viable biomarker. The surfaces were tested using those cell lines at different incubation times. For comparison, surfaces were also functionalized by a similar antibody array and a mixture of PEG and anti-EpCAM.

Figure 3:
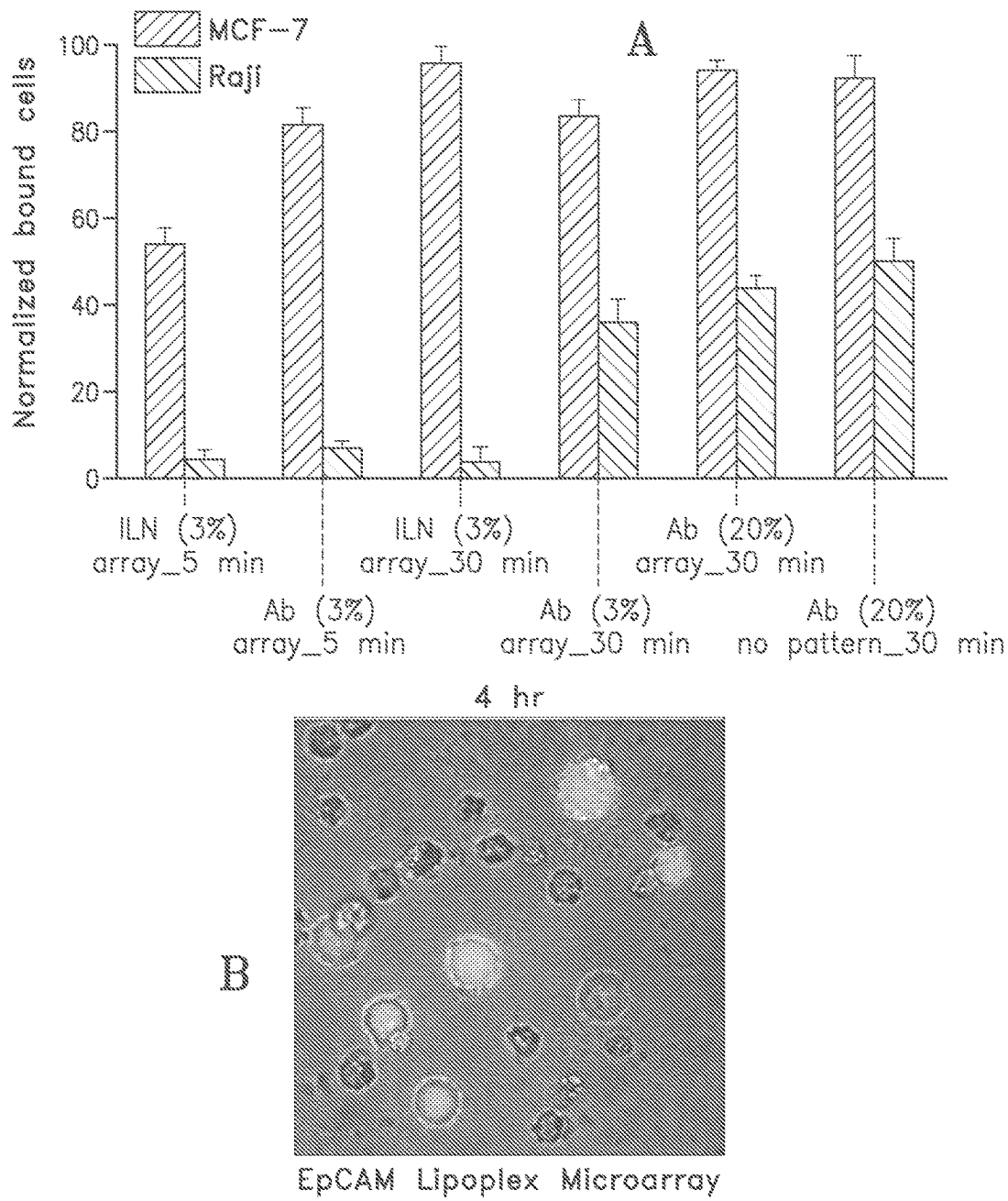
FIG. 3 shows quantitative comparison and micrographs of iTLN capture. (A) Quantitative comparison of MCF-7 cell capture and non-specific binding of Raji cells using EpCAM based iTLN and antibody arrays at different cell incubation times and antibody concentrations. (B) Fluorescence micrograph showing miR-21 detected in captured MCF-7 cells by iTLN microarray containing miR21 LNA MB and EpCAM antibody.
Figure 4:
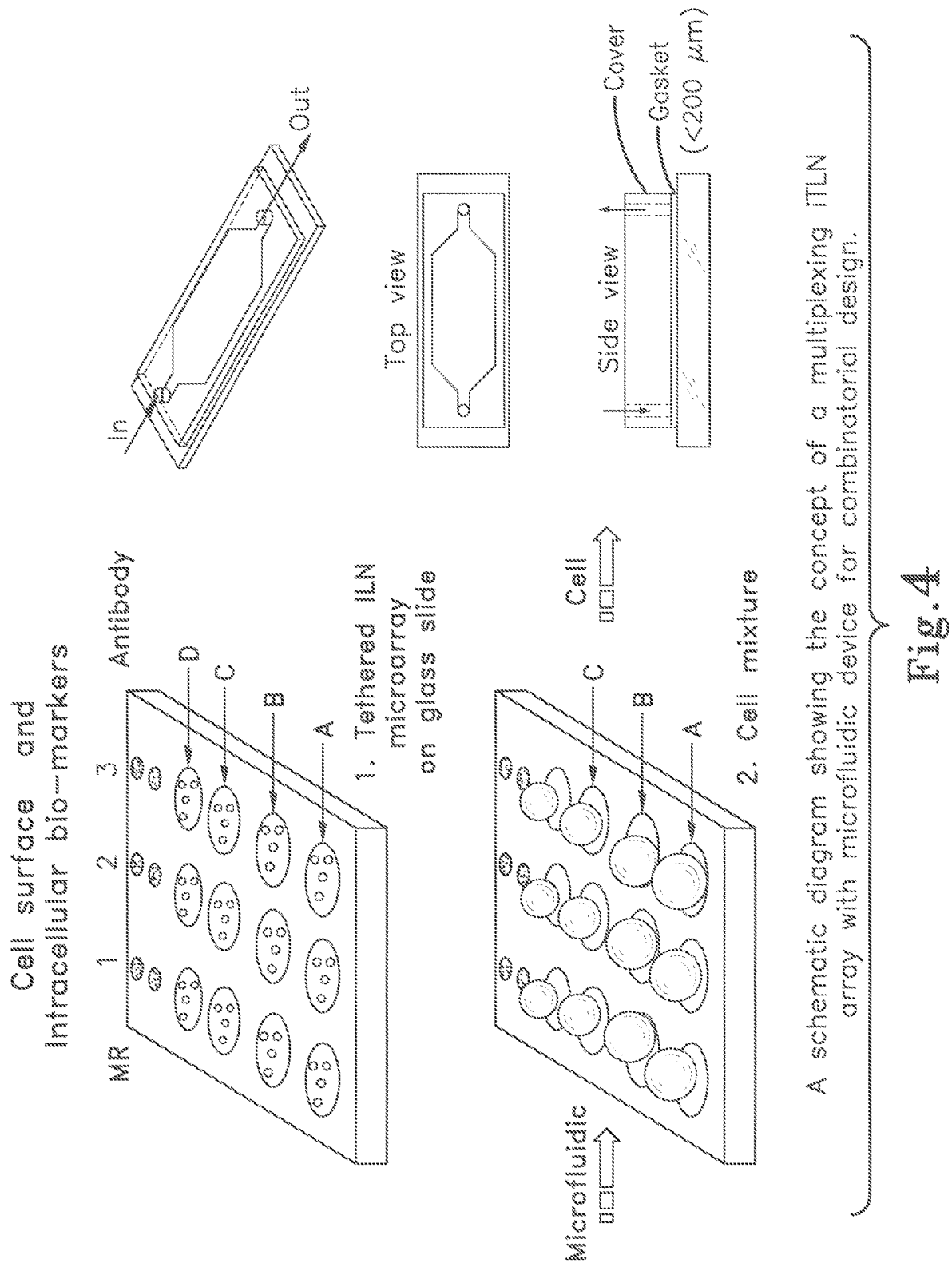
FIG. 4 shows a schematic diagram showing the concept of multiplexing iTLN array for combinatorial design.

FIG. 2E-H shows microscopy images of captured cells on both conventional antibody and iTLN microarrays. It is clear that the efficacy of cell separation is much better in iTLN microarrays. FIG. 3A quantitatively compares the two types of arrays for the MCF-7/Raji cell pair at 5 and 30 min cell incubation time. With the same material composition, the iTLN microarray was able to capture ~95% MCF-7 cells at a washing shear stress of 60 gm when the cell incubation time was 30 min. The capture efficiency dropped to ~55% when the cell incubation time was 5 min. On the other hand, the antibody microarray captured ~80% MCF-7 cells and was insensitive to the cell incubation time. The number of nonspecifically bounded Raji cells was lower in iTLN microarrays, less than 5% for the iTLN microarray, but much higher (>5% and >30%%) for the antibody array at 5 and 30 min incubation time respectively when washed under 60 gm shear stress. These results show that the iTLN microarray can provide better separation efficiency than the antibody microarray.

The performance of surface coated by the anti-EpCAM/PEG mixture was worse than the arrays. FIG. 3A shows that increasing the antibody content from 3 to 20% in antibody microarray and antibody/PEG mixture did not improve the cell separation efficacy because it increased the capture of non-targeted cells.

FIG. 3B shows that the captured cells are able to internalize iTLNs and release the pre-loaded MBs after 4 hours for in-situ detection of miR-21 in MCF-7 cells.

A number of advantages of the iTLN microarray over the conventional microarrays for cell sorting have been demonstrated herein. First, iTLNs with sizes around 100 nm can provide much stronger cell-array interactions compared with adsorbed antibody conformed near the surface with a height around several nanometers.

Second, the strong interactions of lipids with cell surface are an important factor for high cell binding strength. The combined antibody and lipid effects can substantially reduce the amount of ligands required for array production. To achieve equivalent cell capture densities, iTLN microarrays required more than five times less material than antibody immobilization.

Third, the principal components of this platform are the tethered lipoplex by micro-contact printing and post-insertion of cell surface ligands, both are simple and versatile to various lipids and ligands selection.

In addition, sorted cells can uptake iTLNs containing pre-loaded detection reagents and/or drug allowing cell sorting and intracellular bioassaying in one stop, not achievable by any existing assays. Multiplexing of cell surface and intracellular ligands can be easily achieved as in the conventional array design.

Example 4: Tethered Cationic Lipoplex Nanoparticle Chip Containing Molecularprobes for Exosome and Virus Detection In this example, the potential of the cTLN chip in detecting mRNA inside lentivirus for infectious disease warning and circulating microRNA-21 (miR-21) as the biomarker for lung cancer early detection was demonstrated.

Many infectious diseases and even cancer are caused by viral infection. Current virus detection methods, such as ELISA, western blot and qRT-PCR, rely on the detection of the antibodies to the virus or the viral genetic materials (viral mRNA or DNA) in the infected cells. These methods are tedious and time consuming. More importantly, they are indirect methods and cannot directly detect virus and prevent infection. Direct detection of virus is very important since after the original infection, it takes weeks and even months for antibodies to the virus or viral genetic materials to appear in the blood or infected cells. During this window period, the infected person can still spread the disease. A direct and simple detection method is highly desired to capture and characterize the virus itself at very early stage for infectious disease warning.

Figure 5:
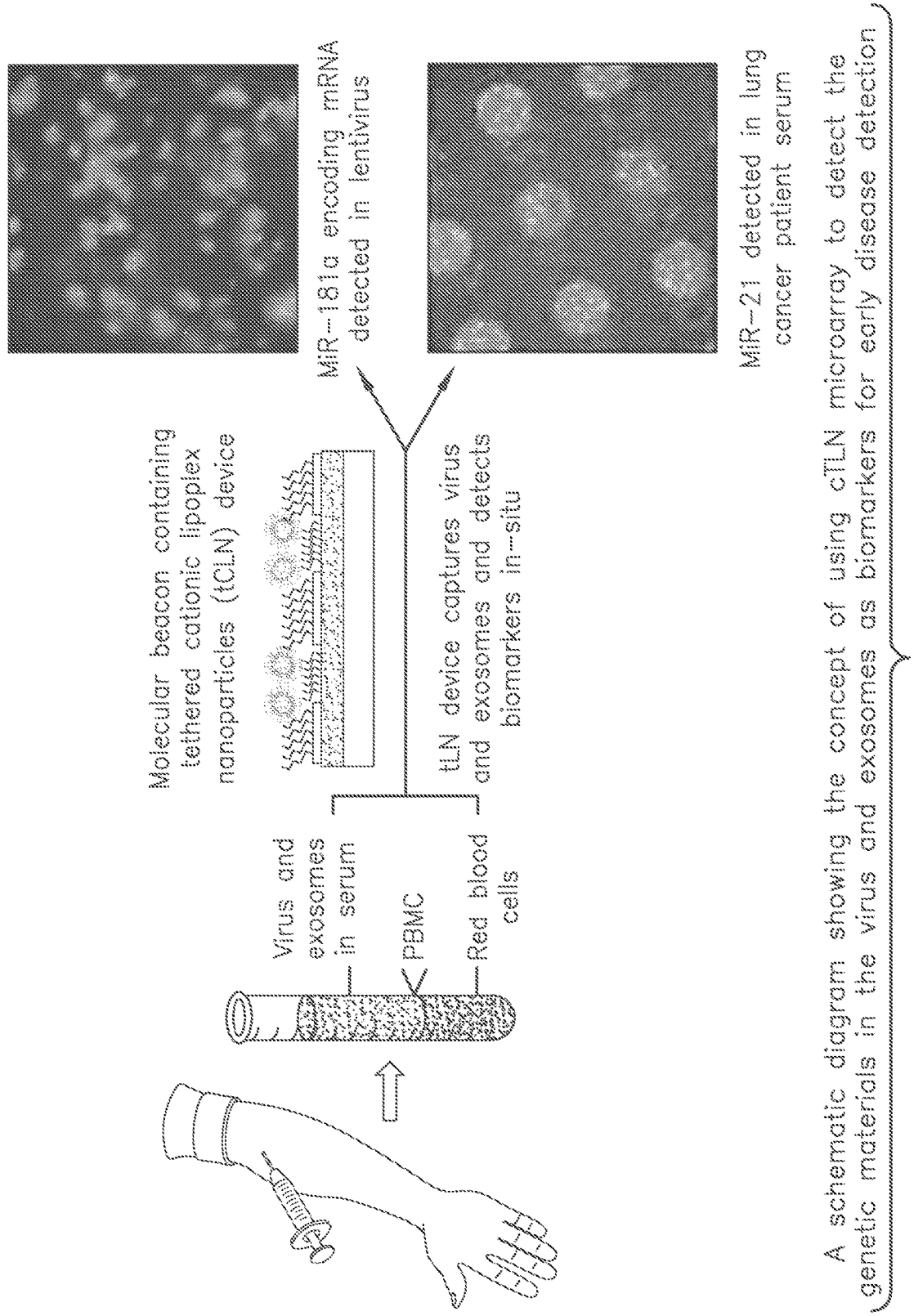
FIG. 5 shows a schematic showing the concept of using iTLN/cTLN microarray to detect the genetic materials in the virus and serum as biomarkers for early disease detection.

Detecting circulating microRNAs released by cancer cells in serum or plasma serves as a useful "liquid biopsy" for cancer early detection and surveillance. Circulating miRNAs are generally packaged in exosomes, protecting them from endogenous RNase activity in the circulation. Circulating exosomal microRNAs are potential indicator because a primary source of circulating exosomal microRNAs in patients with cancer is the tumor. In many cancers, it has been shown that total exosome and exosomal microRNA levels in cancer patients are significantly higher than controls, and the circulating exosomal miRNA patterns may be a potential predictor of the overall survival on cancer patients, suggesting that circulating exosomal microRNAs are used as a diagnostic tool for cancer. The most widely used method for isolating exosomes and characterizing the microRNA expression levels involves a series of centrifugation steps, followed by ultracentrifugation/fractionation in a sucrose gradient. However, it is difficult to obtain high exosome purities greater using this method. The method is also time consuming, and as such, is not readily adaptable to high throughput analyses in clinic use. As shown in FIG. 5, virus or exosome containing serum can be isolated from the whole blood, and then applied on the cTLN chip. Molecular detection probes, such as molecular beacon (MB) in this case, are encapsulated in the cationic lipoplexes to detect the genetic materials in the virus and exosomes as biomarkers for early disease detections. Here, tethered cationic lipoplex nanoparticle (cTLN) chip is made of 10 mg/ml lipids mixture of [1,2-di-O-octadecenyl-3-trimethyl ammonium propane (chloride salt) (DOTMA):Cholesterol:Biotin-methoxy-PEG (MW-2,000 Da)-distearoylphos-phatidyle-thanolamine (biotin-PEG-DSPE)=49:49:2 molar ratio] in ethanol.

To demonstrate the interactions between natural nanoparticles secreted by cells, i.e. virus or exosomes, and the manmade tethered lipoplex nanoparticles disclosed herein, the total internal reflective fluorescence (TIRF) microscope was used to visualize the release and capture of exosomes released by A549 non-small cell lung cancer cells in real time (FIG. 6A). As shown in FIG. 6B, 1 hour after the A549 cells were applied on the tCLN microarray containing miR-21 MB, there were not many green fluorescent signals from miR-21 MB on cTLN chip observed. However, 2 hours later, lots of green fluorescence emitted by miR-21 MB were observed, indicating the successful capture and detection of miR-21 containing exosomes released by A549. In addition, miR-21 MB fluorescence from the A549 cells was observed, indicating that the cTLN chip can detect miR-21 expression in both the exosomes and the cells. Although not explored in this study, the cTLN chip is an excellent tool for many applications, such as to study the cellular response and the change in cell-cell communication to outside stimuli including growth factors or chemotherapeutic drugs.

Then, the biological atomic force microscopy (Bio-AFM) in fluidic condition with PBS buffer solution was used to observe the fusion between exosomes and lipoplex nanoparticles as shown in FIG. 6C.

Figure 7:
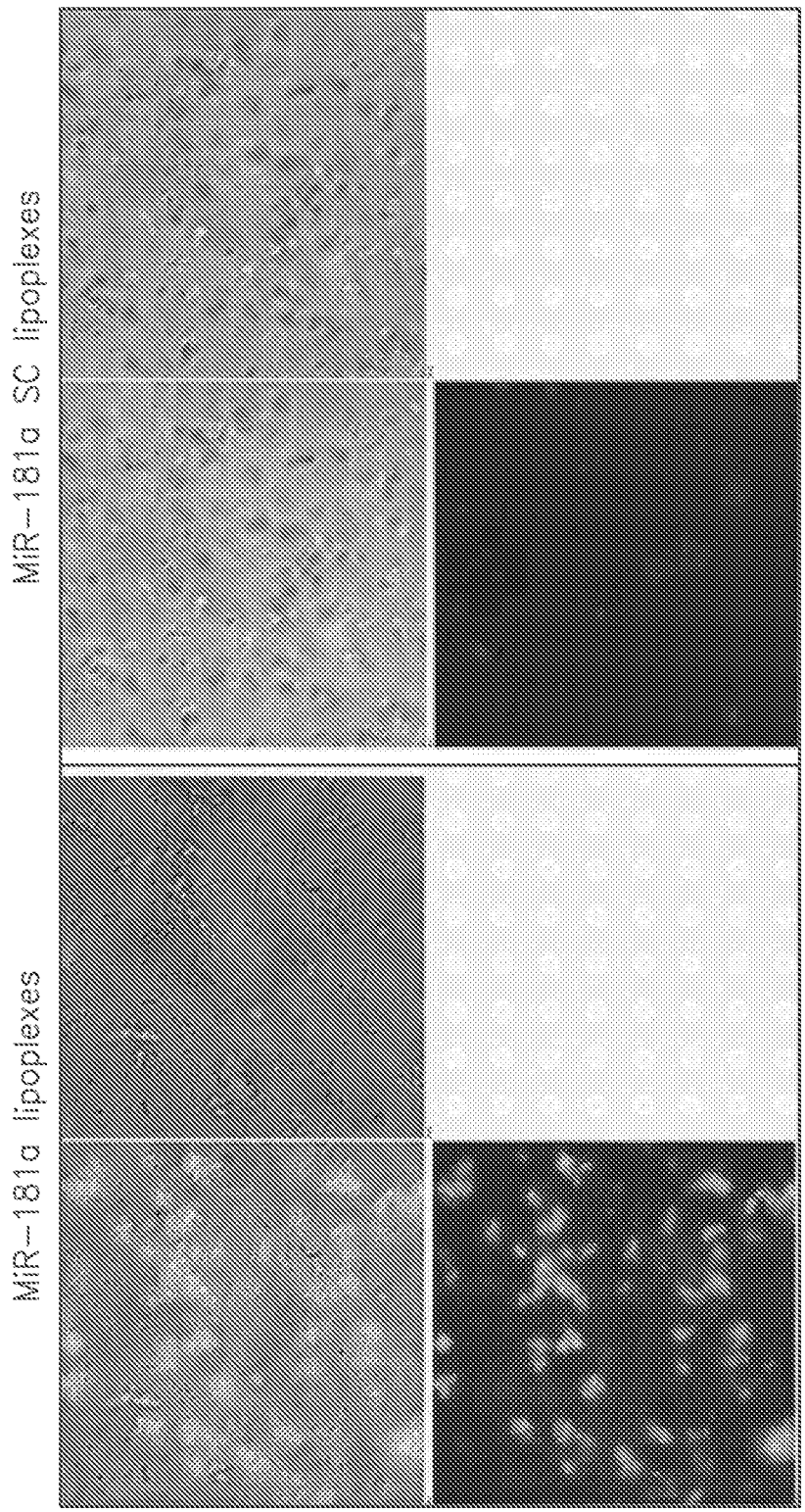
FIG. 7 shows that the green fluorescence from miR-181a MB demonstrates the successful capture and detection of miR-181a mRNA inside the lentivirus using the cTLN chip.

The cTLN method is first demonstrated in lentivirus detection and characterization. MiR-181a MB (5'-FAM BHQ1-3') was encapsulated in cLNs to detect miR-181a encoding mRNA in the lentivirus. MicroRNA-181a encoding lentivirus was applied on cTLN device and incubated at 37° C. for 2 hours. As shown in FIG. 7, the green fluorescence from miR-181a MB demonstrated the successful capture and detection of miR-181a mRNA inside the lentivirus. As expected, miR-181a scramble MB did not show any fluorescent signals. This is the first demonstration of direct capture and characterization of virus simultaneously in one step.

Figure 8:
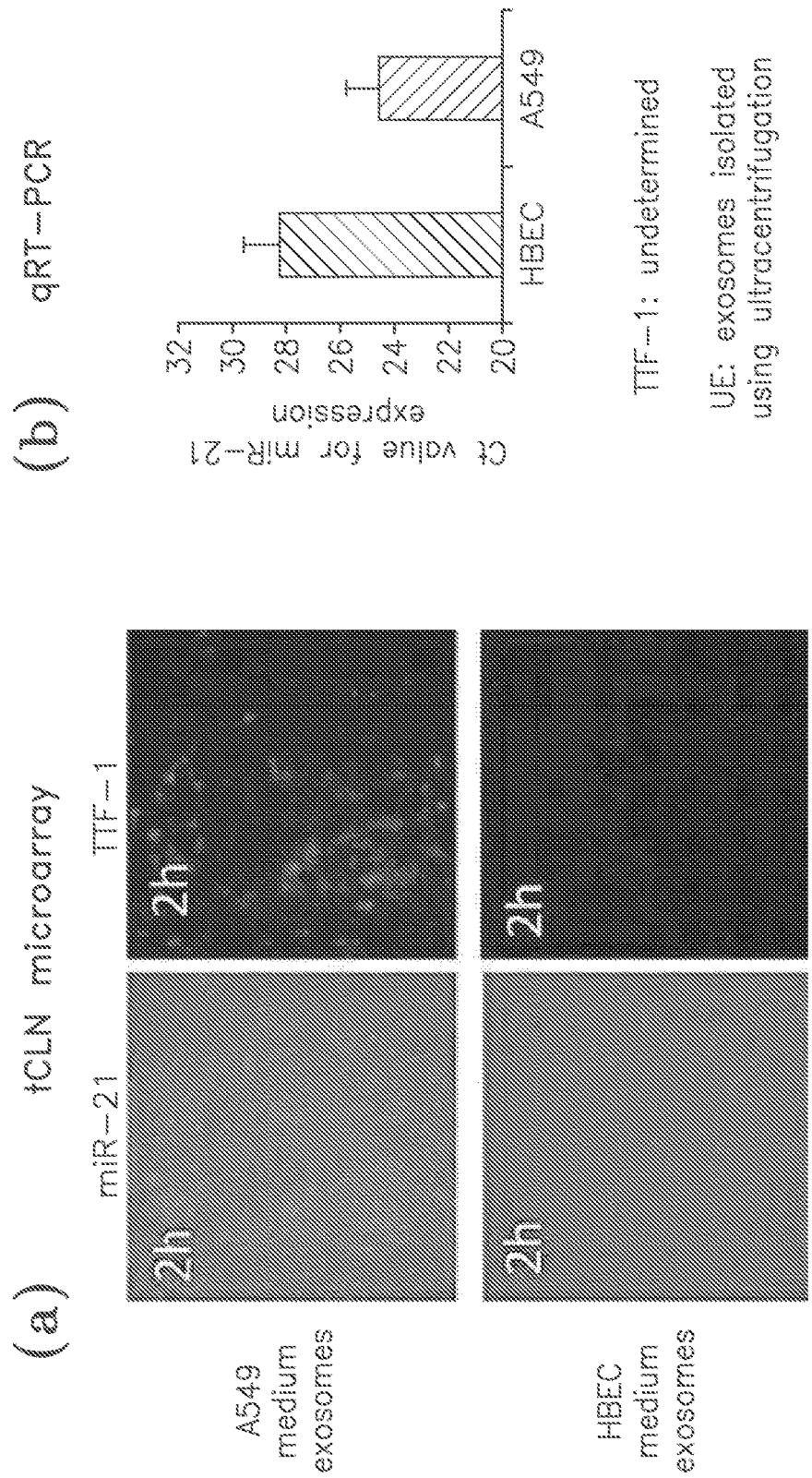
FIG. 8, at part a), shows that the cTLN chip disclosed herein shows stronger fluorescence signals of miR-21 microRNA and TTF-1 mRNA in A549 cancer cell line based culture medium than the normal HBEC lung cell line based culture medium. At part b) of FIG. 8, and comparing to qRT-PCR, the chip disclosed herein has higher sensitivity.

Recent reports showed that changes in the levels of circulating exosomal miR-21 were associated with tumor burden and malignant progression. miR-21 MB and miR-21 scramble MB were encapsulated in the lipoplex nanoparticles to detect miR-21 expression in exosomes. To confirm the lung tumor origin of the exosomes, another MB that detects the thyroid transcription factor-1 (TTF-1) mRNA, a clinical marker of lung adenocarcinoma, was also encapsulated in the lipoplex nanoparticles. First, the cTLN chip was used to detect miR-21 and TTF-1 mRNA in the exosomes secreted by A549 cells and normal human bronchial epithelial cells (HBEC). Exosomes from the culture medium of A549 and HBEC were first isolated using ultracentrifugation. Exosomes were applied on cTLN chip and incubated at 37° C. for 2 hours. As shown in FIG. 8, miR-21 and TTF-1 mRNA expression in exosomes produced by A549 was higher than exosomes secreted by HBEC. Results from qRT-PCR also showed that the miR-21 expression in A549 exosomes was ~12.43 folds higher than HBEC exosomes. However, qRT-PCR was not able to detect TTF-1mRNA expression in both A549 and HBEC exosomes, indicating that cTLN is a more sensitive detection method.

Figure 9:
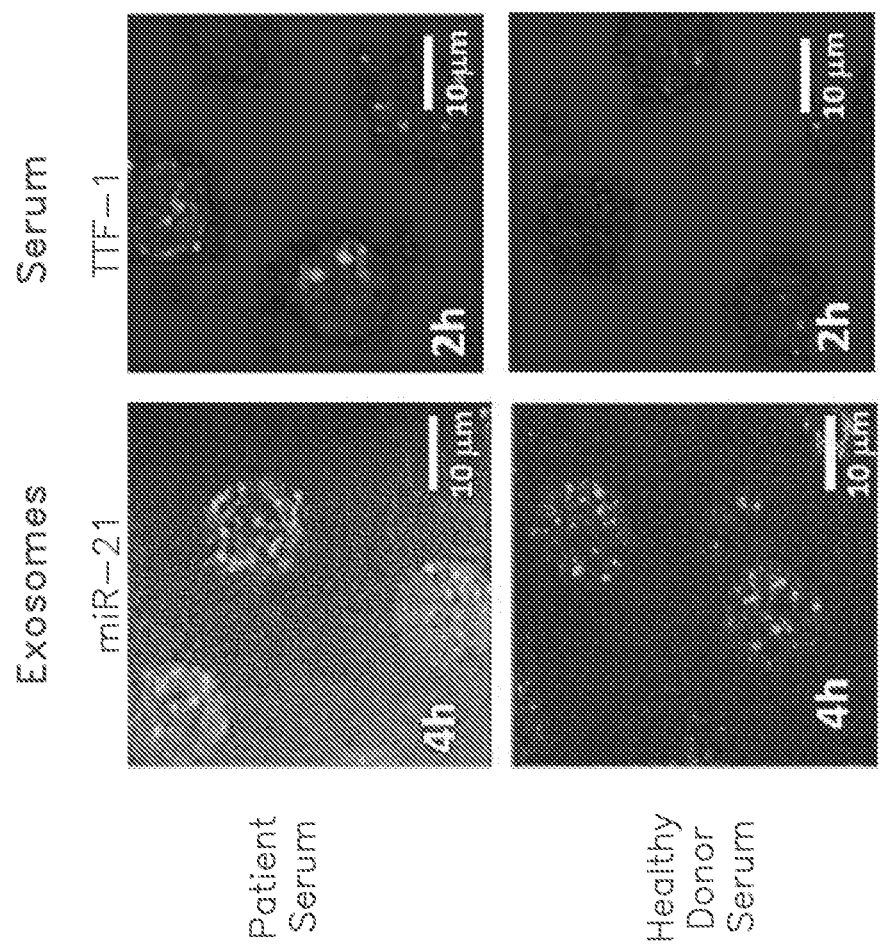
FIG. 9 shows that the chips disclosed herein show stronger fluorescence signals of miR-21 microRNA and TTF-1 mRNA in a lung cancer patient serum than in a healthy human serum.

Then the cTLN chip was tested using serum samples donated from a lung cancer patient and a healthy donor. Exosomes were isolated from the serum samples using ExoQuick™ exosome precipitation solution. Exosomes were then applied on cTLN chip and incubated at 37° C. for 2 hours. In order to determine the capability of cTLN chip to capture and detect exosomes directly from serum, the serum samples were also applied on the cTLN chip without the exosome isolation step. As shown in FIG. 9, the fluorescence signals of MiR-21 and TTF-1 are stronger in patient sample than in the healthy blood.

Example 5: Gold Nanoparticle (Au-NP) Based TLN Method

This example describes a simple method for preparing the Au-NP based TLN method. FIG. 10 shows the schematic of the design concept of the Au-NP based method. Au nanoparticles with diameters ranging from 100 nm to 600 nm were tethered with cationic lipoplex nanoparticles containing molecular beacons (MBs). A 9:1 mixture of 1-thiahexa (ethyleneoxide) lipidic anchor molecule WC14 [20-tetradecyloxy-3,6,9,12,15,18,22-heptaoxahexatricontane-1-thiol] and a biotin-conjugated PEG thiol was formed onto gold nanoparticles as self-assembly monolayer (SAM). Neutravidin was added for 5 min and un-reacted neutravidin was removed by centrifugation. The MBs containing LNs were then added in the neutravidin conjugated Au-NP solution.

As shown in FIG. 11, the fluorescence intensity between a solution-based mixing method with TLNs and exosomes in serum and Au-NP based TLN method is compared quantitatively. The solution-based mixing method showed a weak signal after incubation at 37° C. for 2 hours because of poor fusion between LNs and exosomes in serum. However, the Au-NP based method shows a significant increase of the fluorescence intensity after 2 hours because the LNs tethered on Au-NP efficiently fuse with the target exosomes.

Example 6: Polystyrene Magnetic Beads Based TLN Method

This example describes a simple method for preparing the PS magnetic microbeads as a TLN method. FIG. 10 shows the schematic of the design concept. PS microbeads with diameters ranging from 1 μm to 8 μm were used to tether TLNs. First, PS microbeads were coated with Au-NP of 20 nm diameter in citrus buffer solution or with Au layer of 20 nm using evaporation. A 9:1 mixture of 1-thiahexa(ethyleneoxide) lipidic anchor molecule WC14 [20-tetradecyloxy-3,6,9,12,15,18,22-heptaoxahexatricontane-1-thiol] and a biotin-conjugated PEG thiol was formed onto gold nanoparticles as self-assembly monolayer (SAM). Neutravidin was added for 5 min and un-reacted neutravidin was removed by centrifugation. The MBs containing LNs were then added in the neutravidin conjugated Au-NP solution.

As shown in FIG. 12, the PS magnetic microbeads based method shows a significant increase of the fluorescence intensity after 2 h incubation because the LNs tethered on PS microbeads fuses well with the target exosomes.

This example is aimed at potential applications to single point detection using low-cost detector such as a microplate reader because it is highly valuable for easy clinical diagnosis. A magnet can also be used to concentrate all beads to a single spot and the total fluorescence intensity being detected by a portable UV lamp for point-of-care.

Example 7: cTLN Arrays

Non-invasive early detection methods have the potential to reduce mortality rates of both cancer and infectious diseases. Here, it is shown that tethered cationic lipoplex nanoparticles containing molecular beacons (MBs) can capture cancer cell-derived exosomes or viruses, and identify encapsulated RNAs in a single step. Cationic lipoplex nanoparticles linked onto the surface of a thin glass plate capture negatively charged viruses or cell-secreted exosomes from culture medium or human serum by electrostatic interactions to form larger nanoscale complexes. Lipoplex/virus or lipoplex/exosome fusion leads to mixing of viral/exosomal RNAs and MBs in the lipoplexes. Exosomes enriched in target RNAs are readily identified by specific binding to the MBs. The in situ detection of target extracellular RNAs without diluting the sample leads to high detection sensitivity not achievable by existing methods, e.g. qRT-PCR. The present invention demonstrates this concept for lentivirus and serum from lung cancer patients.

Given their important role in regulating gene expression and recognizing that their dysfunction plays a casual role in human cancers, messenger RNAs (mRNAs) and microRNAs (miRNAs) have emerged as potential biomarkers for cancer detection. Extracellular RNAs have been found to be stable in blood and other bodily fluids, partially attributable to their encapsulation within cell-secreted microvesicles, so-called exosomes. Therefore, capturing these exosomes and quantifying the encapsulated miRNAs and mRNAs is a promising approach to achieving non-invasive assays for cancer detection. Although miRNAs and mRNAs have been quantitatively measured in human serum by qRT-PCR, existing approaches to exosome capture and RNA isolation/concentration have proven to be expensive and time consuming. More importantly, these approaches quantify target RNAs from exosomes secreted by all mammalian cells. Since cancer cell-derived exosomes represent only a small fraction of the microvesicle population in circulation, these approaches lack sensitivity for biomarker detection.

Here, it discloses a new technology, tethered cationic lipoplex nanoparticle (tCLN) biochip, and demonstrates simultaneous exosome capture and quantification of target miRNA and mRNA in serum of lung cancer patients and lentivirus. Lung cancer is the number one cause of cancer related deaths. Sensitive and non-invasive detection modalities can contribute to improved outcomes. In lung cancer, elevated circulating levels of miR-21 have been shown to distinguish patients with malignant solitary pulmonary nodules from those with benign lesions, while Thyroid Transcription Factor-1 (TTF-1) is a well-recognized biomarker in lung cells. Therefore, miR-21 and TTF-1 mRNA were selected as biomarkers to assess the novel assay disclosed herein.

Many infectious diseases and some cancers have been linked to viral infections. Current methods for detecting viral infections, which rely on antibodies against the virus or the presence of viral genetic material, are tedious. It also takes days for those antibodies to appear. Thus, development of a simple detection method for capturing and identifying the virus for early warning of infection is desirable.

Figure 13A:
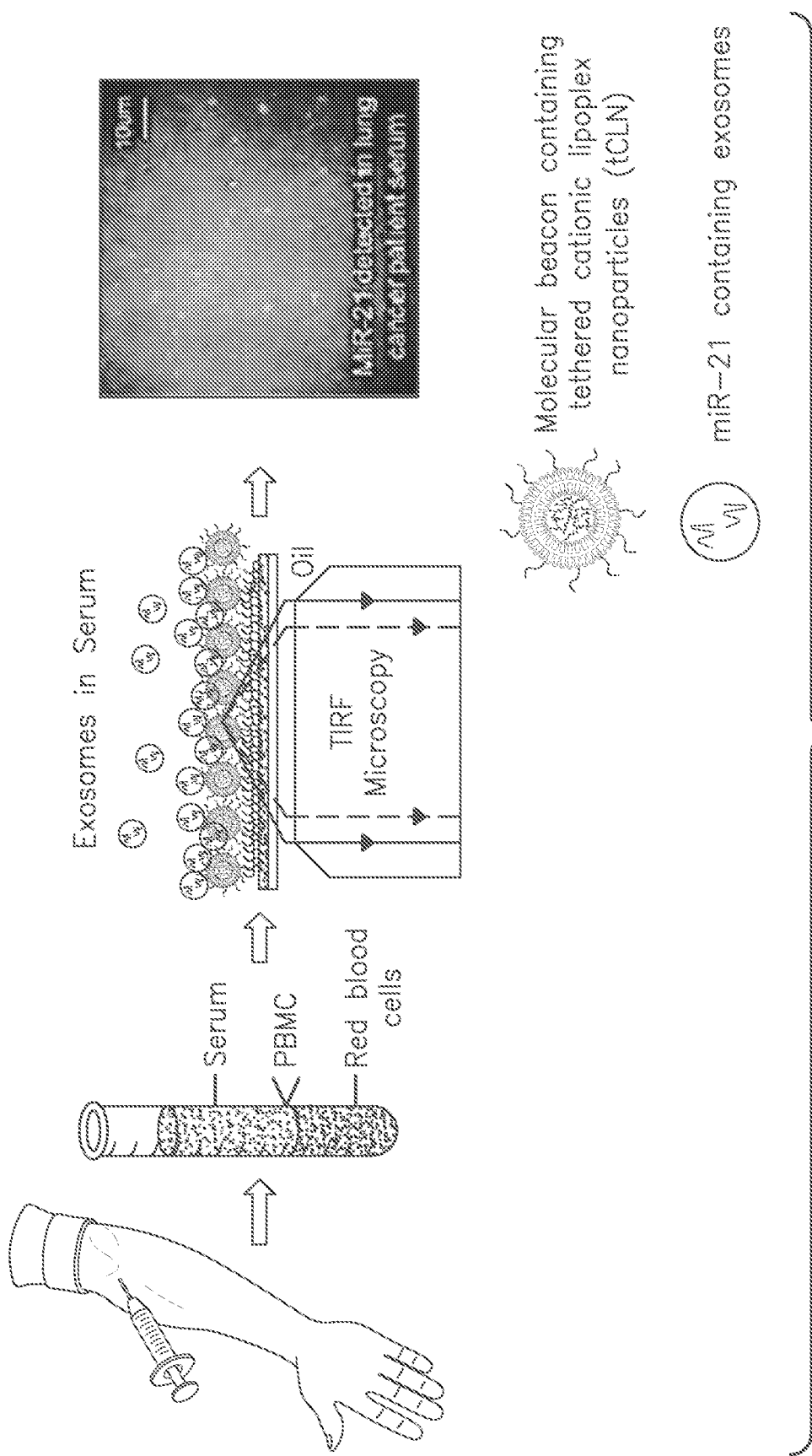
FIGS. 13a through 13c show a tCLN technology overview.
Figure 13B:
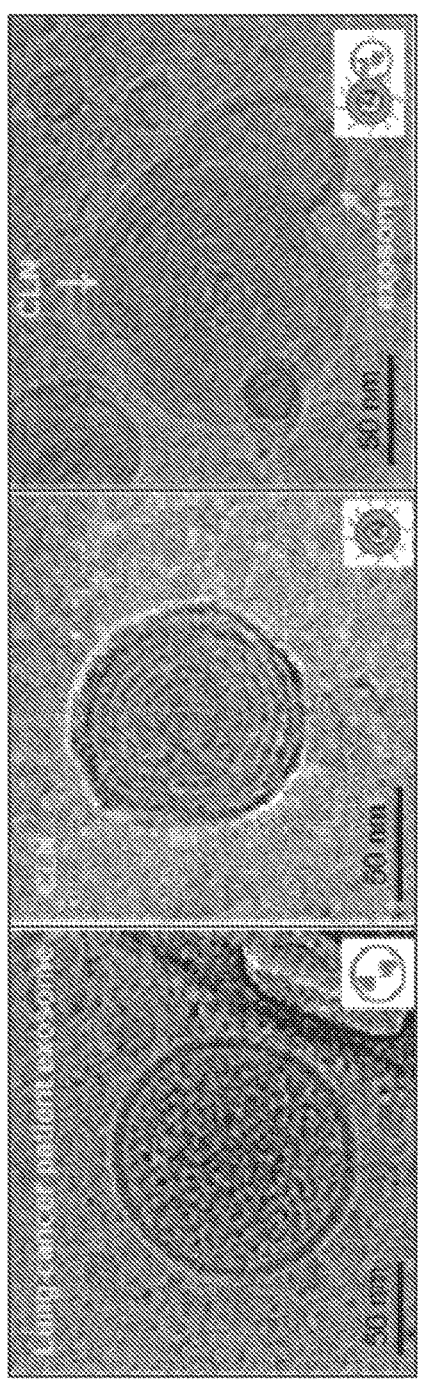

The tCLN biochip is placed on a Total Internal Reflection Fluorescence (TIRF) microscope (FIG. 13a), which allows for the simultaneous capture of exosomes and the in situ analysis of encapsulated RNA targets in a single step without pre- or post-treatment of the sample. Serum can be isolated from the whole blood and then applied directly on the tCLN biochip. Molecular beacons (MBs) are encapsulated in the CLN, which capture the negatively charged exosomes via electrostatic interactions to form larger complexes. Lipoplex-exosome fusion leads to mixing of exosomal RNAs and MBs within the nanoscale confinement of the complexes near the biochip interface (FIG. 13b). Given its high sensitivity and near-interface (~300 nm) detection, TIRF microscopy coupled with the tCLN technology is an ideal modality for detecting RNAs or other genetic materials within the tethered nanoparticles.

Figure 13C:
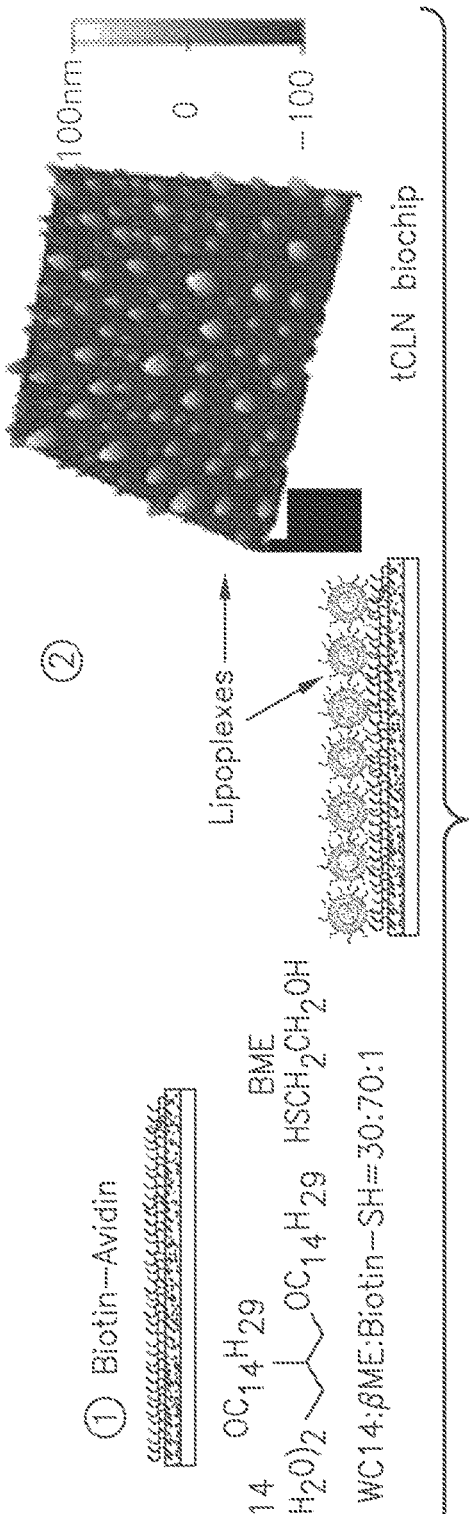

In one aspect, disclosed herein is a simple method for preparing the tCLN biochip (FIG. 13c). MBs are oligonucleotide hybridization probes that can identify the presence of specific nucleic acids. To achieve high stability, locked nucleic acid (LNA) enhanced MBs and nuclease resistant MBs were used to detect specific miRNAs and mRNAs, respectively.

Figure 14A:
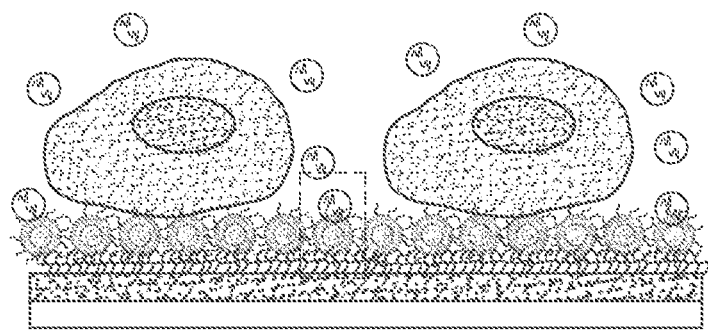
FIGS. 14a through 14e show the characterization of exosome secretion and fusion with tCLN.
Figure 14B:
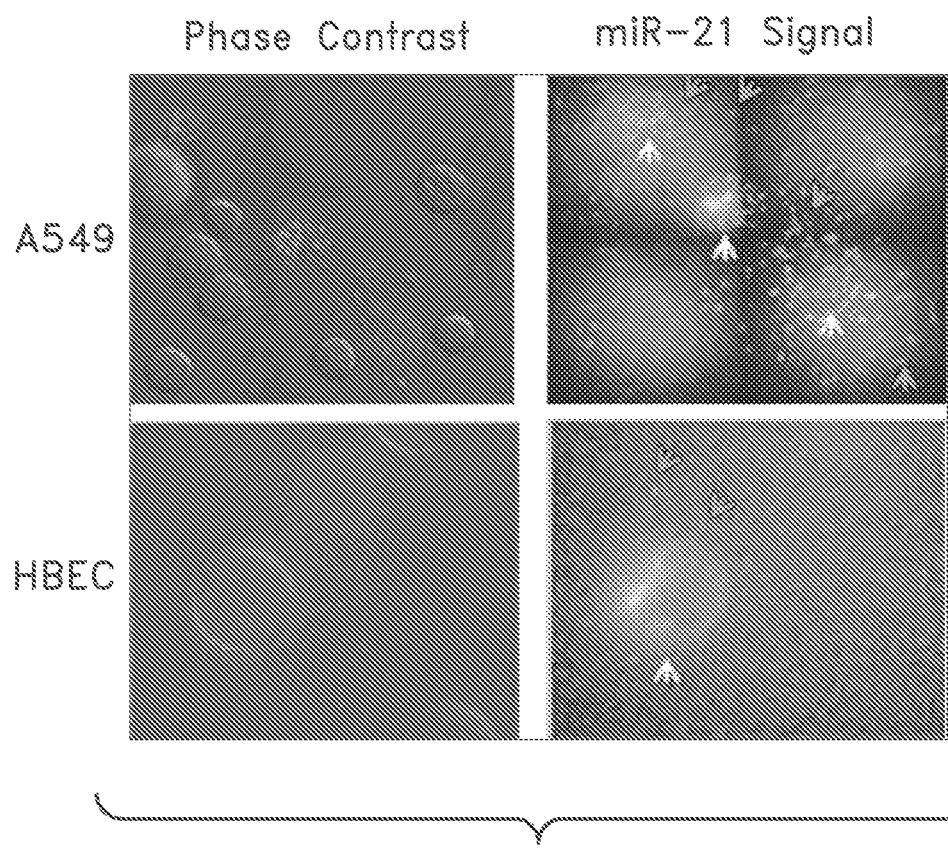

TIRF microscopy was used to visualize the secretion of exosomes by A549 non-small cell lung cancer (NSCLC) cells and their capture by tCLN in a live-cell imaging assay (FIG. 214a). Fluorescent signals from the miR-21-specific MBs were observed from the exosomes released by the cells and inside the cytoplasm (FIG. 14b), indicating that the tCLN biochip can detect the presence of miR-21 in both exosomes and cells. After CLN are internalized by the cells, the subsequent release of the MBs leads to detecting target intracellular RNAs.

Figure 14C:
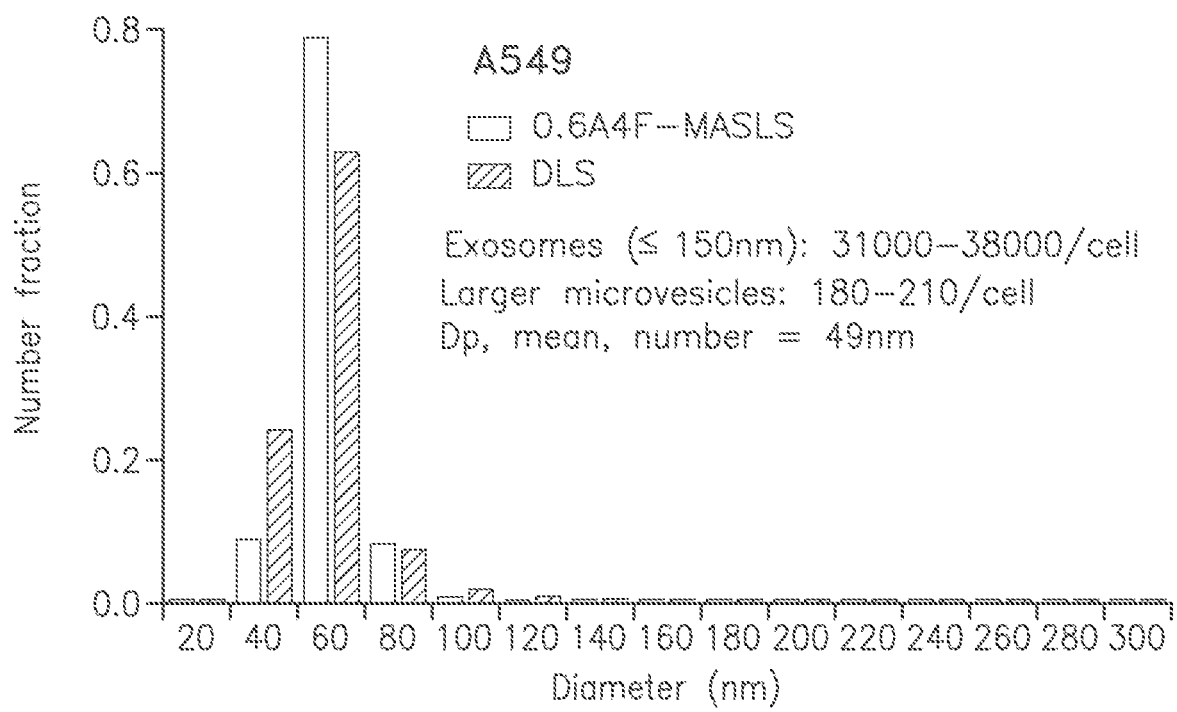
Figure 14D:
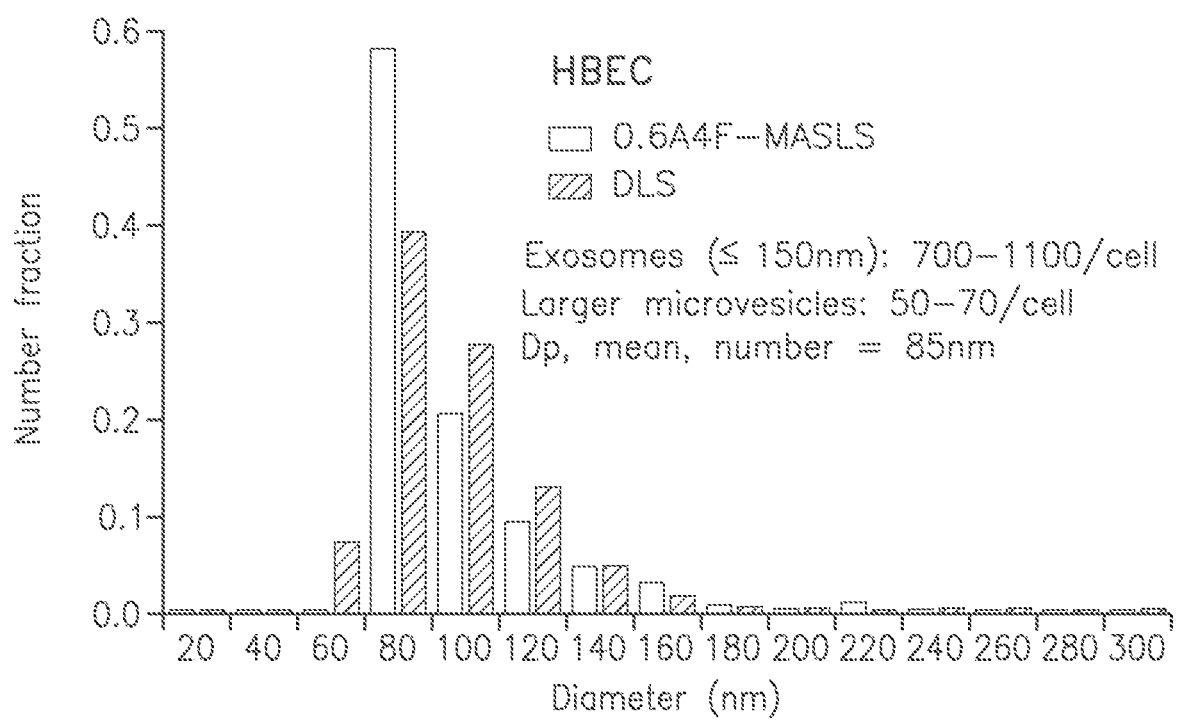
Figure 14E:
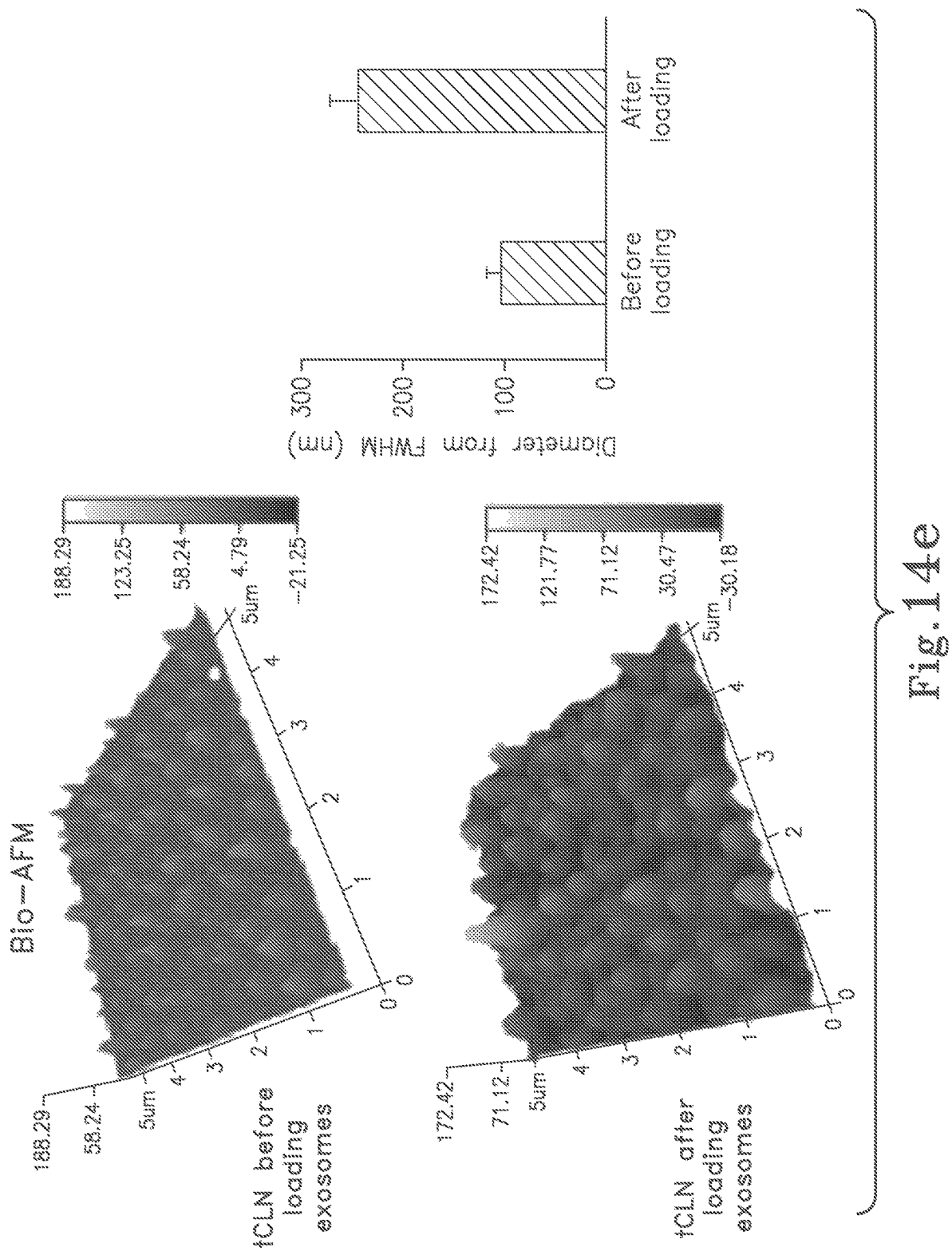

In normal human bronchial epithelial cells (HBEC), there were mainly green fluorescent signals from miR-21-specific MBs observed inside the cells. Using asymmetric flow field flow fractionation coupled with multi-angle static light scattering (A4F-MASLS) and dynamic light scattering (DLS), the number and size distribution of exosomes and larger microvesicles secreted by the two cell types were measured (FIGS. 14c and 14d). A4F-MASLS measurements indicate that A549 cells secrete more exosomes and microvesicles compared to HBEC cells over 48 hours, while the mean diameter by number of A549 exosomes is smaller than that of HBEC.

Biological atomic force microscope (Bio-AFM) measurements of nanoparticle sizes before and after exosome fusion with CLN (FIG. 14d) shows the number of nanoparticles remained the same, but the average diameter of the fused complexes is 2.5 times that of the CLN before fusion, indicating that each CLN captured >10 exosomes. Since the multi-layered CLN contain more cationic lipids (with high zeta potential) than the phospholipids comprising the exosomes, a single lipoplex nanoparticle is able to capture many exosomes.

Figure 15A:
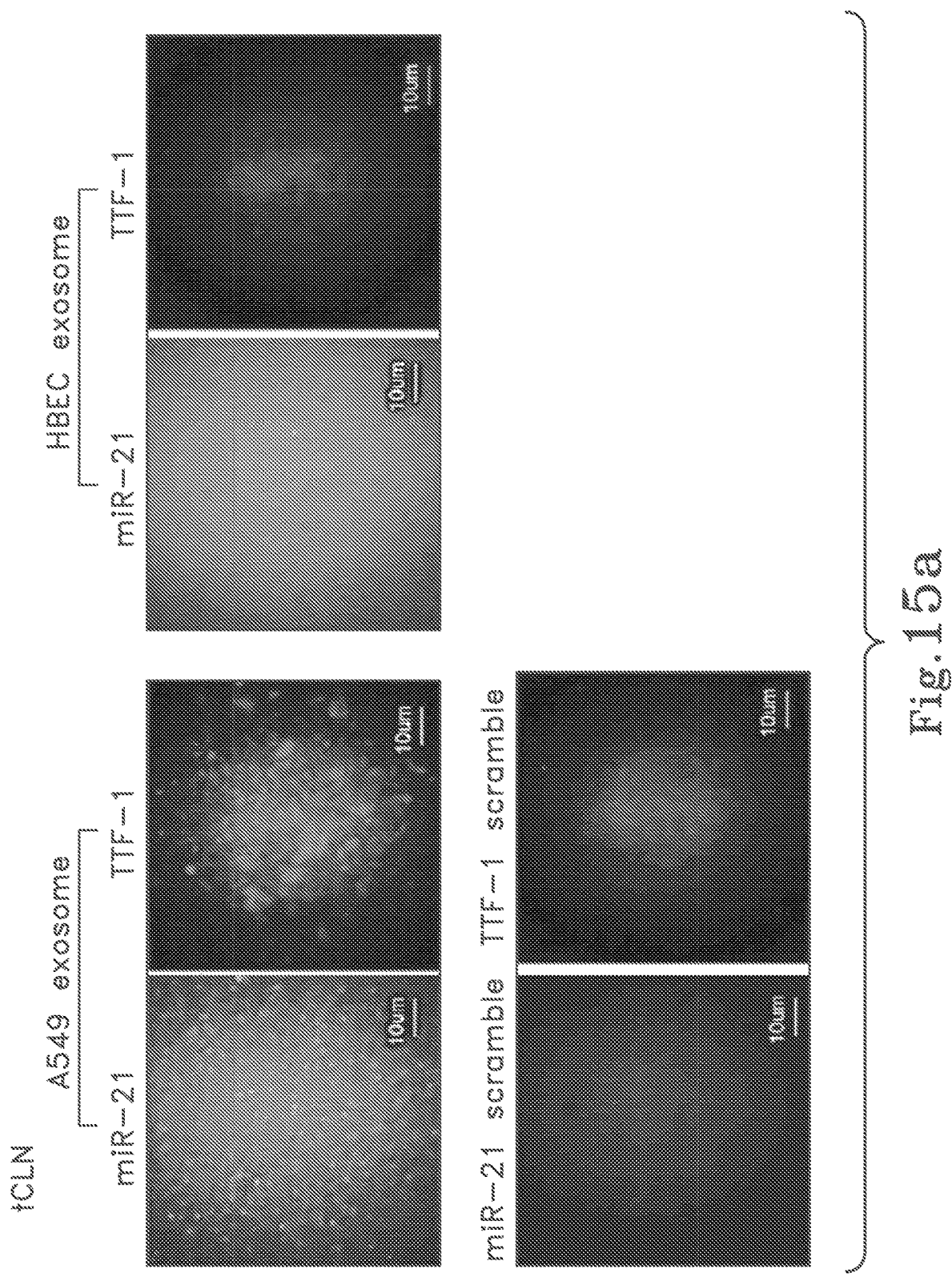
FIGS. 15a through 15e show a comparison of tLCN and qRT-PCR for miRNA and mRNA detection in cell culture medium.
Figures 15B, 15C:
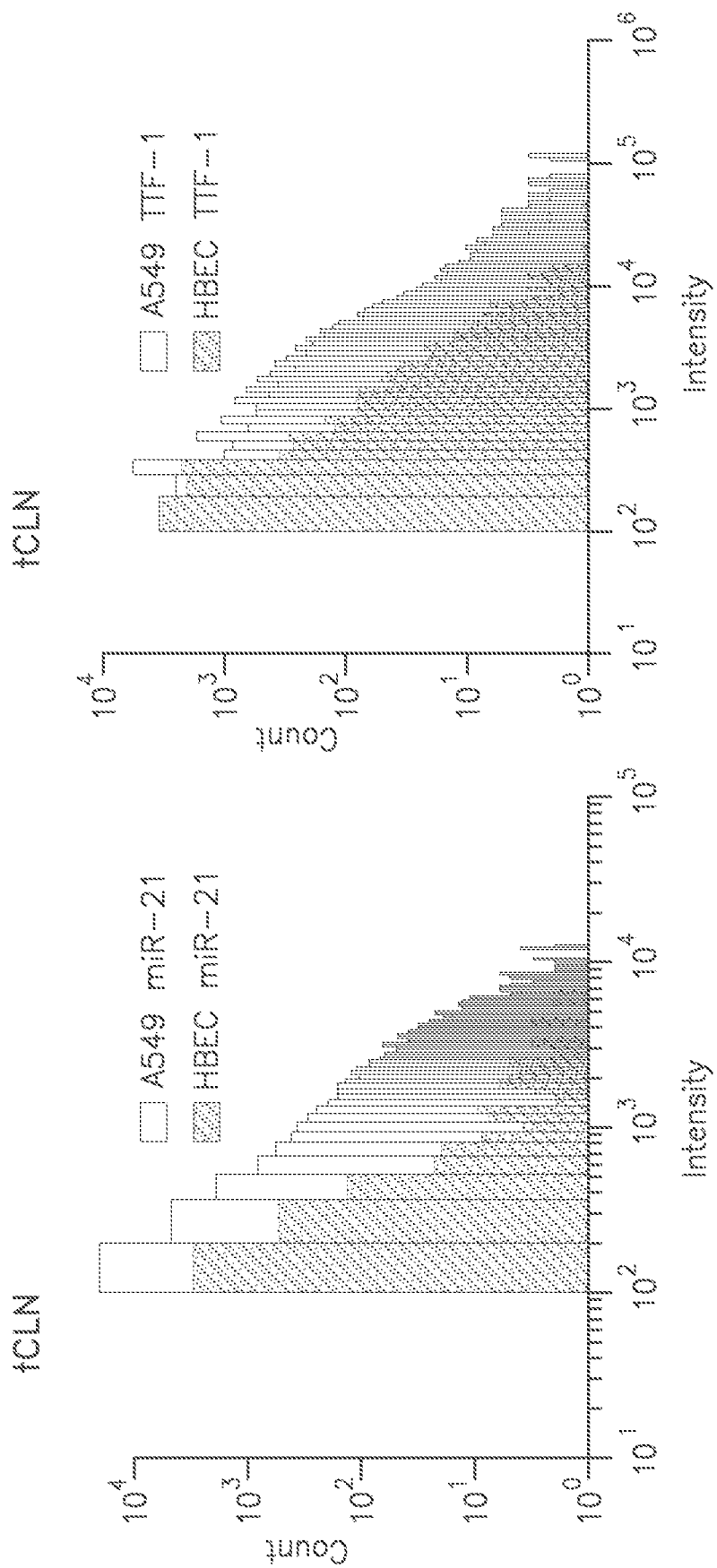
Figure 15E:
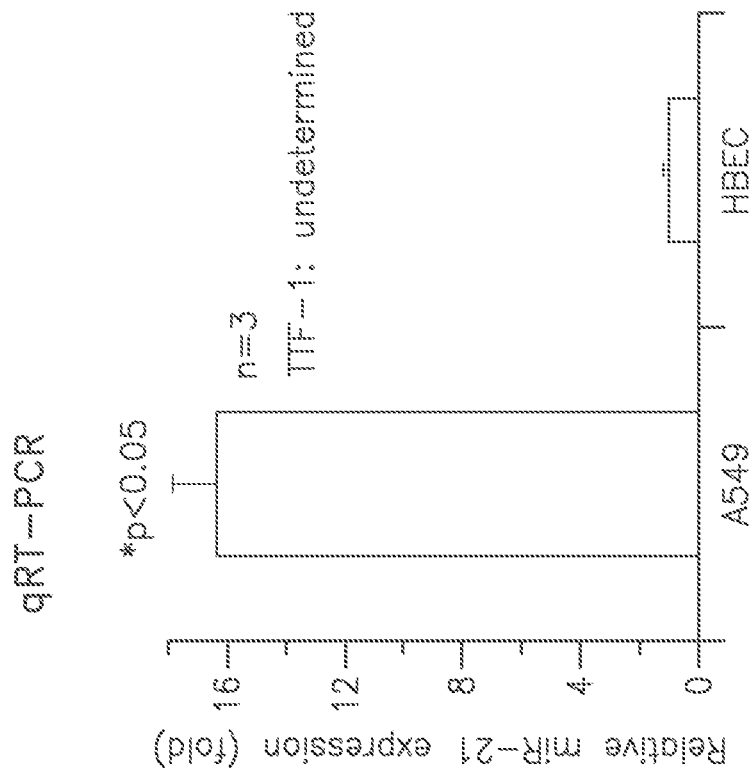
Figure 15D:
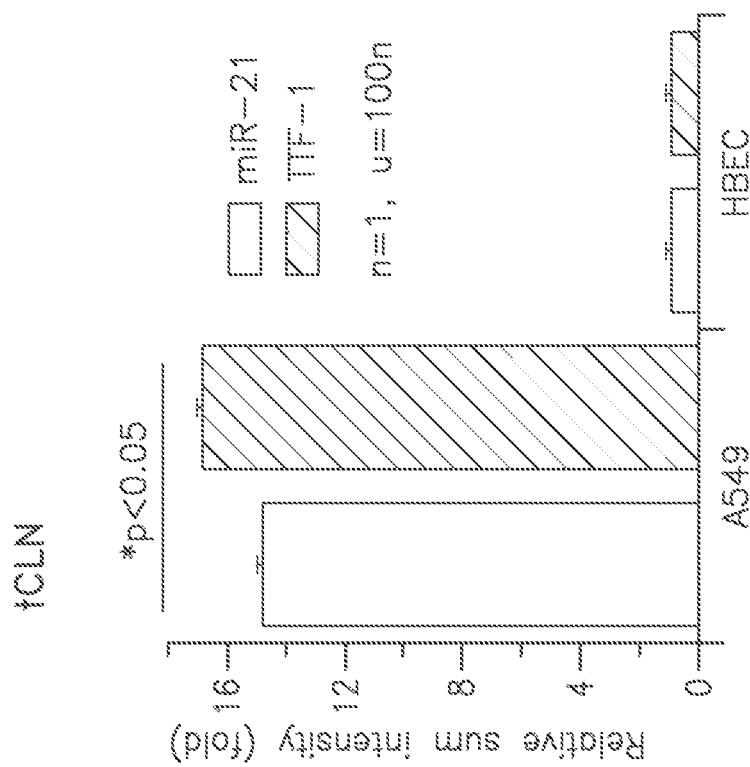

Exosomes collected from A549 and HBEC cell culture medium were applied to the tCLN chip containing both miR-21-specific and TTF-1 mRNA-specific MBs. The A549 exosomes revealed much higher miR-21 and TTF-1 fluorescence signals compared to those for HBEC exosomes (FIG. 15a). Image analysis of fluorescence intensity distributions shows that more A549 exosomes have higher miR-21 and TTF-1 abundances than HBEC exosomes (FIGS. 15b and 15c). The sum of fluorescence intensity in A549 exosomes relative to HBEC exosomes (FIGS. 15d and 15e) confirms that tCLN and qRT-PCR provide comparable results for miR-21 detection. TTF-1 mRNA in the exosomes was not detected by qRT-PCR (FIG. 15e), but was clearly detected using the tCLN biochip. Since the population of exosomes secreted from a cell line is very uniform in fluorescence intensity, a single 80 μm×80 μm image containing ~$10^5$ CLN (~$10^6$ exosomes) is sufficient to provide a consistent result. FIG. 15d shows that the variation among 100 images is small.

Then the tCLN biochip was tested using serum samples from 4 lung cancer patients and 2 normal donors. Exosomes isolated from the serum samples using ExoQuick™ exosome precipitation solution were applied on tCLN biochip and incubated at 37° C. for 2 hours. The serum samples were also directly applied on tCLN biochip without the exosome isolation step. The miR-21 and TTF-1 fluorescence signals were stronger in the patient samples compared to normal donors (FIG. 16a. The fluorescence intensity distributions also indicate that patient samples have more exosomes with higher miR-21 and TTF-1 abundance than samples from normal donors (FIG. 16b). Higher miR-21 and TTF-1 abundance in the patient serum samples is likewise measured without exosome isolation (FIG. 16c).

Exosomes in human serum samples come from various cell types. Consequently, more images (i.e. more exosomes) are required to provide a meaningful average signal (FIG. 16c). However, the trend between patient and normal donor samples remained the same when fewer images were used for the analysis.

In qRT-PCR, total RNA is isolated from all exosomes in a sample. Thus, RNA from disease-specific exosomes are mixed with exosomes from a myriad of other cell sources, and diluted in the RNA isolation steps, thereby diminishing the sensitivity of target RNA detection (FIG. 16d).

In tCLN, the exosomal content is confined within the lipoplex-exosome complex, which circumvents dilution. In addition, RNA detection is based on analyzing images in which each exosome-lipoplex cluster can be quantitatively evaluated individually for target RNA abundance above a specified cutoff level. This focusing effect can better distinguish cancer cell-derived exosomes from other exosomes because the former is more likely to contain many target RNAs leading to a strong local fluorescence signal. Cryo-TEM images (FIG. 13b) reveal that many exosomes secreted by A549 cells and lung cancer patient #4 contain more material than most exosomes secreted by HBEC cells, indicating that the over-representation of target RNAs in exosomes secreted from cancer cells provides sensitive biomarkers for extracellular cancer detection. To demonstrate this 'focusing' effect by tCLN, exosomes secreted from A549 cells were spiked into exosomes isolated from the normal donor serum. The tCLN assay can detect the spiked exosomes secreted from <$10^4$ tumor cells (FIG. 16e), while qRT-PCR is insensitive below $10^7$ tumor cells (FIG. 16f). Comparing FIGS. 16c and 16e, it is speculated that the miR-21 and TTF-1 signals observed in lung cancer patients #3 (early stage) and #4 (late stage) come from the exosomes secreted by ~$2\times10^4$ and ~$10^7$ cancer cells respectively.

The tCLN biochip is a simple and affordable tool for identifying low-level RNA targets that are important for early cancer and disease detection. It can be extended to a multiplexing array design in which specific MB mixtures are spatially separated on the biochip to allow the detection of multiple targets for RNA profiling.

The invention claimed is:

1. A method for detecting the presence or absence of a selected disease or condition in a subject from a sample of tissue or body fluid of the subject, comprising the steps of:
providing a lipoplex nanoparticle, comprising a liposome having at least one molecular probe incorporated therein and at least one modification of the surface of the liposome to facilitate the surface for binding to a target feature that is characteristic of the presence or absence of the selected disease or condition, the lipoplex nanoparticle being tethered to a substrate;
contacting the lipoplex nanoparticle with an amount of the sample from the subject; and
detecting excitation of a label of the at least one molecular probe, the excitation occurring from the capture and incorporation into the lipoplex nanoparticle of the target feature;
wherein the target feature is selected from the group consisting of: a cell-secreted extracellular vesicle and a virus.

2. The method of claim 1, wherein:
the lipoplex nanoparticle is an immunolipoplex nanoparticle and the at least one surface modification is selected from the group consisting of: an antibody, a peptide, a carbohydrate, and combinations thereof.

3. The method of claim 2, wherein the at least one surface modification is an antibody on the surface of the liposome that is specific for a determinant on the target feature.

4. The method of claim 1, wherein:
the lipoplex nanoparticle is a cationic lipoplex nanoparticle and the at least one surface modification comprises a positive charge on the surface of the liposome for binding negatively charged moieties in the sample from the subject.

5. The method of claim 1, wherein:
the at least one molecular probe comprises a molecular beacon.

6. The method of claim 5, wherein:
the molecular beacon comprises a fluorescence marker or a radiomarker.

7. The method of claim 1, wherein:
the step of detecting excitation is achieved by an instrument selected from the group consisting of: a total internal reflective fluorescence microscope, a fluorescence microscope, a plate reader and a portable fluorescence detector.

8. The method of claim 1, wherein:
at least some of the tethered lipoplex nanoparticles are further modified on the surface of the liposome with a positive charge for binding negatively charged particles in the sample from the subject.

9. The method of claim 4, wherein:
at least some of the tethered cationic nanoparticles are further modified on the surface of the liposome with at least one surface modification selected from the group consisting of: an antibody, a peptide, a carbohydrate, and combinations thereof.

10. A method for detecting the presence or absence of a selected disease or condition in a subject from a sample of tissue or body fluid of the subject, comprising the steps of:
providing a biochip comprising a substrate on which at least one array of lipoplex nanoparticles are tethered; each array comprising a plurality of the lipoplex nanoparticles that comprise a liposome having at least one molecular probe incorporated therein and at least one modification of the surface of the liposome to facilitate the surface for binding to a target feature that is characteristic of the presence or absence of the selected disease or condition;
contacting the biochip with an amount of the sample from the subject; and
detecting excitation of the molecular probe of at least one of the arrays, the excitation occurring from the capture and incorporation into the lipoplex nanoparticle of the target feature;
wherein the target feature is selected from the group consisting of: a cell-secreted extracellular vesicle and a virus.

11. The method of claim 10, wherein:
the biochip comprises at least two arrays that differ from each other in that a first of the arrays comprises lipoplex nanoparticles with a first modification of the liposome surface and at least one further array comprises lipoplex nanoparticles with a second modification of the liposome surface that is different from the first modification.

12. The method of claim 11, wherein:
the at least two arrays further differ in that the first of the arrays comprises lipoplex nanoparticles with a first molecular probe and the at least one further array comprises lipoplex nanoparticles with a second molecular probe that is different from the first labeling moiety, such that the excitations of the respective molecular probes are distinct.

13. The method of claim 11, wherein:
each of the at least two arrays further differ from each other in size or shape so as to be visually distinct.

* * * * *